(12) United States Patent
Schwartz et al.

(10) Patent No.: US 6,670,393 B2
(45) Date of Patent: *Dec. 30, 2003

(54) CARBAMATE-BASED CATIONIC LIPIDS

(75) Inventors: David Aaron Schwartz, Encinitas, CA (US); Bob Dale Brown, Encinitas, CA (US); Brian Patrick Dwyer, San Diego, CA (US)

(73) Assignee: Promega Biosciences, Inc., Madison, WI (US)

( * ) Notice: Subject to any disclaimer, the term of this patent is extended or adjusted under 35 U.S.C. 154(b) by 66 days.

This patent is subject to a terminal disclaimer.

(21) Appl. No.: 09/892,058

(22) Filed: Jun. 25, 2001

(65) Prior Publication Data

US 2003/0097011 A1 May 22, 2003

Related U.S. Application Data

(60) Division of application No. 08/665,057, filed on Jun. 5, 1996, now Pat. No. 6,251,939, which is a continuation-in-part of application No. 08/483,465, filed on Jun. 7, 1995, now abandoned.

(51) Int. Cl.[7] ................. A61K 31/215; C07C 57/03; C07C 271/06
(52) U.S. Cl. ................. 514/506; 554/227; 560/159
(58) Field of Search ................. 554/227; 560/159

(56) References Cited

U.S. PATENT DOCUMENTS

| | | | | |
|---|---|---|---|---|
| 3,649,674 A | * | 3/1972 | Hoyer et al. | 260/482 |
| 4,007,281 A | | 2/1977 | Bauman | |
| 4,680,290 A | | 7/1987 | Cassal | |
| 4,816,567 A | | 3/1989 | Cabilly et al. | |
| 4,897,355 A | | 1/1990 | Eppstein et al. | |
| 5,171,678 A | | 12/1992 | Behr et al. | |
| 5,214,136 A | | 5/1993 | Lin et al. | |
| 5,264,618 A | | 11/1993 | Felgner et al. | |
| 5,283,185 A | * | 2/1994 | Epand et al. | 435/173.2 |
| 5,334,761 A | | 8/1994 | Gebeyehu et al. | |
| 5,336,615 A | | 8/1994 | Bell et al. | |
| 5,399,346 A | | 3/1995 | Anderson et al. | |
| 6,020,317 A | * | 2/2000 | Junichi et al. | 514/44 |

FOREIGN PATENT DOCUMENTS

| | | |
|---|---|---|
| EP | 0 051 873 | 5/1982 |
| EP | 0 330 191 B1 | 8/1989 |
| EP | 336779 | 10/1989 |
| EP | 414963 | 3/1991 |
| EP | 414963 A1 * | 6/1991 |
| JP | 01261383 | 10/1989 |
| JP | 05295017 | 11/1993 |
| WO | WO 86/05518 | 9/1986 |
| WO | WO 87/01728 | 3/1987 |
| WO | WO 88/01304 | 2/1988 |
| WO | WO 89/01940 | 3/1989 |
| WO | WO 89/12060 | 12/1989 |
| WO | WO 90/15065 | 12/1990 |
| WO | WO 91/06556 | 5/1991 |
| WO | WO 91/06626 | 5/1991 |
| WO | WO 91/06629 | 5/1991 |
| WO | WO 91/08213 | 6/1991 |
| WO | WO 91/13080 | 9/1991 |
| WO | WO 91/15500 | 10/1991 |
| WO | WO 91/18997 | 12/1991 |
| WO | WO 92/02258 | 2/1992 |
| WO | WO 92/05186 | 4/1992 |
| WO | WO 92/09705 | 6/1992 |
| WO | WO 92/14843 | 9/1992 |
| WO | WO 92/19637 | 11/1992 |
| WO | WO 92/20702 | 11/1992 |
| WO | WO 92/20822 | 11/1992 |
| WO | WO 92/20823 | 11/1992 |
| WO | WO 93/09127 | 5/1993 |
| WO | WO 93/10820 | 6/1993 |
| WO | WO 93/12135 | 6/1993 |
| WO | WO 93/24507 | 12/1993 |
| WO | WO 93/24508 | 12/1993 |
| WO | WO 93/24640 A2 | 12/1993 |
| WO | WO 93/24640 A3 | 12/1993 |
| WO | WO 94/00569 | 1/1994 |
| WO | WO 94/12629 | 6/1994 |
| WO | WO 94/19314 * | 9/1994 |
| WO | 94/19314 | 9/1994 |
| WO | WO 94/21807 | 9/1994 |
| WO | 94/27627 | 12/1994 |

OTHER PUBLICATIONS

Bangham, A. et al., *M. Mol. Biol.* 23:238, 1965.
Behr, J.P., *Acc Chem. Res.* 26, 274, 1993.
Callahan, *Proc. Natl. Acad. Sci.*, 82:732, 1985.
Clivio, et al., *Tet Lett.,* 33:65, 1992.
Clivio, et al., *Tet. Lett.,* 33:69, 1992.

(List continued on next page.)

Primary Examiner—Barbara P. Badio
(74) Attorney, Agent, or Firm—Michael Best & Friedrich LLP; Grady J. Frenchick

(57) ABSTRACT

The present invention provides novel carbamate-based cationic lipids of the general structure:

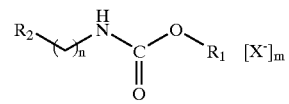

or a salt, or solvate, or enantiomers thereof, wherein (a) $R_1$ is a lipophilic moiety; (b) $R_2$ is a positively charged moiety; (c) n is an integer from 1 to 8; (d) X is an anion or polyanion; and (e) m is an integer from 0 to a number equivalent to the positive charge(s) present on the lipid. The present invention further provides compositions of these lipids with polyanionic macromolecules, methods for interfering with protein expression in a cell utilizing these compositions, and a kit for preparing the same.

4 Claims, 7 Drawing Sheets

OTHER PUBLICATIONS

Clusel, *Nucl. Acids Res.,* 21:3405, 1993.
Connolly, et al., *Nucl. Acids. Res.,* 17:49757, 1989.
Felgner et al., *Proc. Nat. Acad. Sci.,* 84:7413–7417, 1987.
Felgner, *J. Biol. Chem.* 269:2550, 1994.
Fukunaga, M. et al., *Endocrinol,* 115:757, 1984.
Gao, X. and Huang, L., *Biochim. Biophys. Res. Commun.* 179:280, 1991.
Gershon, *Biochem.,* 32:7143, 1993.
Green, *Ann. Rev. Genet.,* 20:671, 1986.
Guy–Caffey et al., "Novel Polyaminolipids Enhance the Cellular Uptake of Oligonucleotides", *Journal of Biological Chemistry,* vol. 270, No. 52, pp. 31391–31395, Dec. 29, 1995.
Jacques et al., "Enantiomers, Racemates and Resoluations", Kreiger, Malabar, FL, 1991 Contents Only.
Kim, S. et al., *Biochim. Biophys. Acta,* 728:339, 1983.
Lin et al., *Science,* 246:1023, 1989.
Maddon et al., *Cell,* 47:333, 1986.
Mayer, L. et al., *Biochim. Biophys. Acta,* 858:161, 1986.
Mayhew E. et al., *Biochim. Biophys. Acta,* 775:169, 1984.
Mizel, *FASEB J.,* 3:2379, 1989.
Moelling, et al., *J. Virol.,* 32:370, 1979.
Nabel, *Human Gene Ther.,* 3:649, 1992.
Nabel, Proc. *Natl. Acad. Sci.,* 90:11307, 1993.
Nikiforov et al., *Tet. Lett.,* 32:2505, 1991.
Nikiforov, et al., *Tet. Lett.,* 33:2379, 1992.
Olson, F. et al., *Biochim. Biophys. Acta,* 557:9, 1979.
Smith, et al., *Ann. Rev. Genet.,* 23:527, 1989.
Strauss, *EMBO J.,* 11:417, 1992.
Szoka, F. et al., *Proc. Natl. Sci.,* 75:4194, 1978.
Uhlmann, *Chem. Rev.,* 90:543, 1990.
Uzé, et al., *Cell,* 60:225, 1990.
Wagner, *Science,* 260:1510, 1993.
Xu, et al., *Tet. Lett.,* 32:2817, 1991.
Zhou, X., et al., *Biochim. Biophys. Acta* 1065:8, 1991.

* cited by examiner 4-1:((3-b-cholest-5-en-3-ol, 2-(dimethylamino)-
ethyl methylphosphonate)

4-2:((3b)-Cholest-5-en-3-ol,2-((2,5-diamino-1-oxopentyl)amino)
ethyl methylphosphonate, dihydrochloride)

4-3:N-a-(6-carboxyspermino)-N,N-dioctadecylglutamic
acid-g-amide, tetra(trifluoroacetate)

FIG. 6a.

| COS-7 CELLS | DELIVERY 3498 | T'FECTION TIME | Delivery 3498PS | T'FECTION TIME | DELIVERY 3793-2 | T'FECTION TIME |
|---|---|---|---|---|---|---|
| *COMMERCIAL LIPIDS* | | | | | | |
| LIPOFECTAMINE | 4,5* | 5hr | 3*,4* | 5hr | 5* | 5hr |
| LIPOFECTIN | 1,1* | 5hr | 4*,5* | 5hr | 0* | 5hr |
| TRANSFECTAM | 5 | 5hr | 5(9:1), | 5hr | 5* | 5hr |
| NOVEL LIPIDS | | | | | | |
| 1-2/4-1 | 2.5 | 5hr | | | | |
| 1-2 | 2.5 | 5hr | 3 | 5hr | | |
| DOPE | 0 | 4hr | | | | |
| GC12/1-2 | 2 | 5hr | 2 | 5hr | | |
| GC21/1-2 | 3 | 5hr | 3.5 | 5hr | | |
| 3-1 | 0 | 4hr | | | | |
| 3-1/DOPE | 0 | 4hr | | | | |
| 3-4 | 1 | 4hr | | | | |
| 3-4/DOPE | 2 | 4hr | | | | |
| 3-3 | 2.5 | 5hr | | | | |
| 3-3/DOPE | 2.5 | 4hr | | | | |

DELIVERY= NUCLEAR FLUORESCENCE

FIG. 6b.

| | DELIVERY 3498 | T'FECTION TIME | DELIVERY 3498PS | T'FECTION TIME | DELIVERY 3793-2 | T'FECTION TIME | |
|---|---|---|---|---|---|---|---|
| SNB 19 | | | | | | | |
| *COMMERCIAL LIPIDS* | | | | | | | |
| TRANSFECTAM | 5 | 5hr | VARIES | 5hr | 4,5 | 5hr | *=9:1 lipid:oligo |
| LIPOFECTAMINE | 4 | 5hr | 4* | 5hr | 4,5 | 5hr | |
| LIPOFECTIN | 1 | 5hr | 4* | 5hr | 1 | 5hr | |
| *NOVEL LIPIDS* | | | | | | | |
| 1-2/4-1 | 1 | 5hr | 4* | 5hr | | | |
| 1-2/4-2 | 1 | 5hr | 1* | 5hr | | | |
| 1-2/4-3 | 3 | 5hr | 2* | 5hr | | | |
| HeLa CELLS | | | | | | | |
| *COMMERCIAL LIPIDS* | | | | | | | |
| TRANSFECTAM | 3 | 5hr | | | | | |
| LIPOFECTAMINE | 3 | 5hr | | | | | |
| LIPOFECTIN | 1 | 5hr | | | | | |
| *NOVEL LIPIDS* | | | | | | | |
| 1-2/4-1 | 0 | 5hr | | | | | |
| HT1080 | | | | | | | |
| *COMMERCIAL LIPIDS* | | | | | | | |
| TRANSFECTAM | 3 | 5hr | | | | | |
| LIPOFECTAMINE | 2 | 5hr | | | | | |
| LIPOFECTIN | 1 | 5hr | | | | | |
| *NOVEL LIPIDS* | | | | | | | |
| 1-2/4-1 | 0 | 5hr | | | | | |

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (xi) SEQUENCE DESCRIPTION: SEQ ID NO: 1:

GCCUAUUUCC CUAUUUCCCU AAAGGGUUUA UUGAGAAUA                      39

(2) INFORMATION FOR SEQ ID NO: 2:

(i) SEQUENCE CHARACTERISTICS:
       (A) LENGTH: 120 base pairs
       (B) TYPE: nucleic acid
       (C) STRANDEDNESS: single
       (D) TOPOLOGY: linear (xi) SEQUENCE DESCRIPTION: SEQ ID NO: 2:

ACCUGGCCUA UUUCCCUAAA GGUGAGUGAC UAACUAAGUC GACUGCAGAC           50

UAGUCAUUGA UUGAGUGUAA CAAGACCGGA UAUCUUCGAA CCUCUCUCUC          100

UCUCUCAGGG UUUAUUGAGA                                          120

(2) INFORMATION FOR SEQ ID NO: 3:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 3:

Met Glu Lys Lys Ile Ser Gly Tyr Thr Thr
 1               5                   10

(2) INFORMATION FOR SEQ ID NO: 4:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (xi) SEQUENCE DESCRIPTION: SEQ ID NO: 4:

UUUUCAGGAG CUAAGGAAGC UAAAAUGGAG AAAAAAAUCA CUGGAUAUAC CACC      54

(2) INFORMATION FOR SEQ ID NO: 5:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 5:

-continued

```
Met Glu Lys Lys Ile Ser Gly Tyr Thr Thr
1               5                   10
```

(2) INFORMATION FOR SEQ ID NO: 6:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 6:

AGUGCAGGA GCUAAGGAAG CUACCAUGGA GAAGAAGAUC ACUGGAUAUA CCACC    54

CARBAMATE-BASED CATIONIC LIPIDS

CROSS-REFERENCE TO RELATED APPLICATIONS

This application is a divisional of U.S. application Ser. No. 08/665,05 , filed Jun. 5, 1996 now U.S. Pat. No. 6,251,939; which is a continuation-in-part of U.S. patent application Ser. No. 08/483,465, entitled "Novel carbamate-Based Cationic Lipids", filed Jun. 7, 1995, now abandoned.

TECHNICAL FIELD OF THE INVENTION

The present invention relates to the field of cationic lipid compounds and their uses including the delivery of macromolecules into cells.

BACKGROUND OF THE INVENTION

None of the following discussion of the background of the invention is admitted to be prior art to the invention.

Lipid aggregates, such as liposomes, have been previously reported to be useful as agents for the delivery of macromolecules (such as DNA, RNA, oligonucleotides, proteins, and pharmaceutical compounds) into cells. In particular, lipid aggregates, which include charged as well as uncharged lipids, have been described as being especially effective for delivering polyanionic molecules to cells. The reported effectiveness of cationic lipids may result from charge interactions with cells which are said to bear a net negative charge. It has also been postulated that the net positive charge on the cationic lipid aggregates may enable them to bind polyanions, such as nucleic acids. For examples, lipid aggregates containing DNA have been reported to be effective agents for efficient transfection of cells.

The structure of a lipid aggregate depends on factors which include composition of the lipid and the method of forming the aggregate. Lipid aggregates include, for example, liposomes, unilamellar vesicles, multilamellar vesicles, micelles and the like, and may have particle sizes in the nanometer to micrometer range. Various methods of making lipid aggregates have been reported in the art. One type of lipid aggregate includes phospholipid containing liposomes. An important drawback to the use of this type of aggregate as a cell delivery vehicle is that the liposome has a negative charge that reduces the efficiency of binding to a negatively charged cell surface. It has been reported that positively charged liposomes that are able to bind DNA may be formed by combining cationic lipid compounds with phospholipids. These liposomes then be utilized to transfer DNA into target cells. (See, e.g. Felgner et al., *Proc. Nat. Acad. Sci.* 84:7413–7417, 1987; Eppstein et al. U.S. Pat. No. 4,897,355; Felgner et al. U.S. Pat. No. 5,264,618; and Gebeyehu et al. U.S. Pat. No. 5,334,761).

Known cationic lipids include N[1-(2,3-dioleoyloxy) propyl]-N,N,N-trimethyl-ammonium chloride ("DOTMA"). Combinations of DOTMA with dioleoylphosphatidyletha-nolamine ("DOPE") have been commercially available. Formulation of DOTMA, either by itself or in 1:1 combination with DOPE, into liposomes by conventional techniques has been reported. However, compositions comprising DOTMA have been reported to show some toxicity to cells.

Another commercially available cationic lipid, 1,2-bis (oleoyloxy)-3,3-(trimethylammonia)propane ("DOTAP") differs from DOTMA in structure in that the oleoyl moieties are linked by ester, rather than ether, linkages to the propylamine. See Figure. However, DOTAP is reported to be more readily degraded by target cells. Other cationic lipids which represent structural modifications of DOTMA and DOTAP have also been reported.

Other reported cationic lipid compounds include those in which carboxyspermine has been conjugated to one of two types of lipids and includes compounds such as 5-carboxyspermylglycine dioctaoleoylamide ("DOGS") and dipalmitoyl-phosphatidylethanolamine 5-carboxyspermyl-amide ("DPPES") (See, e.g. Behr et al., U.S. Pat. No. 5,171,678).

Another reported cationic lipid composition is a cationic cholesterol derivative ("DC-Chol") which has been formulated into liposomes in combination with DOPE. (See, Gao, X. and Huang, L., *Biochim. Biophys. Res. Commun.* 179:280, 1991). For certain cell lines, these liposomes were said to exhibit lower toxicity and provide more efficient transfection than the DOTMA-containing compositions.

Lipopolylysine, made by conjugating polylysine to DOPE has been reported to be effective for transfection in the presence of serum. (Zhou, X. et al., *Biochim. Biophys. Acta* 1065:8, 1991).

However, of the cationic lipids which have been proposed for use in delivering macromolecules to cells, no particular cationic lipid has been reported to work well with a wide variety of cell types. Since cell types differ from one another in membrane composition, different cationic lipid compositions and different types of lipid aggregates may be effective for different cell types, either due to their ability to contact and fuse with target cell membranes directly or due to different interactions with intracellular membranes or the intracellular environment. For these and other reasons, design of effective cationic lipids has largely been empirical. In addition to content and transfer, other factors believed important include, for example, ability to form lipid aggregates suited to the intended purpose, toxicity of the composition to the target cell, stability as a carrier for the macromolecule to be delivered, and function in an in vivo environment. Thus, there remains a need for improved cationic lipids which are capable of delivering macromolecules to a wide variety cell types with greater effeciency.

SUMMARY OF THE INVENTION

In one aspect of the present invention novel carbamate-based cationic lipids having the structure:

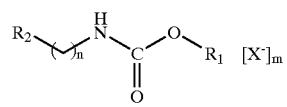

or a salt, or solvate, or enantiomers thereof are provided wherein; (a) $R_1$ is a lipophilic moiety; (b) $R_2$ is a positively charged moiety; (c) n is an integer from 1 to 8; (d) $X^-$ is an anion or polyanion; and (e) m is an integer from 0 to a number equivalent to the positive charge(s) present on the lipid.

In one embodiment $R_1$ may be selected from a variety of lipophilic moieties including a straight chain alkyl of 1 to about 24 carbon atoms, a straight chain alkenyl of 2 to about 24 carbon atoms, a symmetrical branched alkyl or alkenyl of about 10 to about 50 carbon atoms (preferably 25–40), an unsymmetrical branched alkyl or alkenyl of about 10 to about 50 carbon atoms, a steroidyl moiety, a glyceryl derivative or $CH(R_3R_4)$, wherein $R_3$ and $R_4$ are independently a straight chain alkyl moiety of about 10 to about 30 carbon atoms, or a branched alkyl moiety of about 10 to about 30 carbon atoms.

Preferably when $R_1$ is a steroidyl moiety it is a cholesteryl moiety or a non-cholesteryl moiety.

In a prefered embodiment $R_1$ is 3-(1,2-diacyl)propane 1,2-diol moiety or a 3-(1,2-dialkyl)propane 1,2-diol moiety. In particular when $R_1$ is a 3-(1,2-diacyl)propane 1,2-diol moiety itmis preferable that the diacyl group be alkanoic acid of about 10 to about 30 carbon atoms or an alkenoic acid of about 10 to about 30 carbon atoms. When $R_1$ is 3-(1,2-dialkyl)propane 1,2-diol moiety it is preferable that the alkyl moieties be an alkyl group of about 10 to about 30 carbon atoms or an alkenyl group of about 10 to about 30 carbon atoms.

When $R_1$ is a glyceryl derivative it is prefered that it be a 3-O-1,2-diacylglyceryl moiety or a 3-O-1,2-dialkylglyceryl moiety. In particular, when $R_1$ is a 3-O-1,2-diacylglyceryl moiety it is preferable that the diacyl group be an alkanoic acid of about 10 to about 30 carbon atoms or an alkenoic acid of about 10 to about 30 carbon atoms.

It is particularly prefered that when a moiety contains an alkanoic acid that the acid be stearic and when a moiety contains an alkenoic acid that the acid be palmitoic acid or oleic acid.

In another prefered $R_1$ is 18-pentatriacontane, 3-(3β)-cholest-5-ene, or 3-(1,2 distearyl)propane 1,2-diol.

In another embodiment $R_2$ may be selected from a variety of positively charged moieties including an amino acid residue having a positively charged group on the side chain, an alkylamine moiety of about 3 to about 10 carbon atoms, a fluoroalkylamine moiety, or a perfluoroalkylamine moiety of 1 to about 6 carbon atoms, an arylamine moiety or an aralkylamine moiety of 5 to about 10 carbon atoms, a guanidinium moiety, an enamine moiety, an aromatic or non-aromatic cyclic amine moiety of 3 to about 9 carbon atoms, an amidine moiety, an isothiourea moiety, a heterocyclic amine moiety, or a heterocyclic moiety or an alkyl moiety of 1 to about 6 carbon atoms substituted with a substituent selected from the group consisting of $NH_2$, $C(=O)NH_2$, $NHR_6$, $C(=O)NHR_6$, $NHR_6R_7$, or $C(=O)NHR_6R_7$, wherein $R_6$ and $R_7$ are independently selected from an alkyl moiety of 1 to about 24 carbon atoms, an alkenyl moiety of 2 to about 24 carbon atoms, an aryl moiety of about 5 to about 20 carbon atoms, and an aralkyl moiety of about 6 to about 25 carbon atoms.

Preferably when $R_2$ is an amino acid residue it is a lysine, arginine, histidine, ornithine, or an amino acid analog. In particular, it is prefered that the amino acid residue be 3-carboxyspermidine, 5-carboxyspermidine, 6-carboxyspermine or monoalkyl, dialkyl or peralkyl substituted derivatives which are substituted on one or more amine nitrogens with an alkyl group of 1 to about 6 carbon atoms.

It is further preferred that n be an integer from 2 to 6, or more preferably from 2 to 4 and that $X^-$ be a pharmaceutically acceptable anion or polyanion.

In a particularly prefered embodiment the carbamate-based cationic lipid has the structure

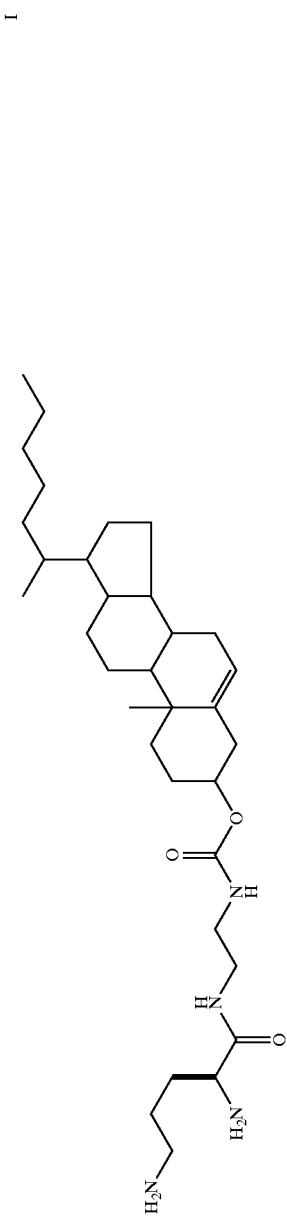
I
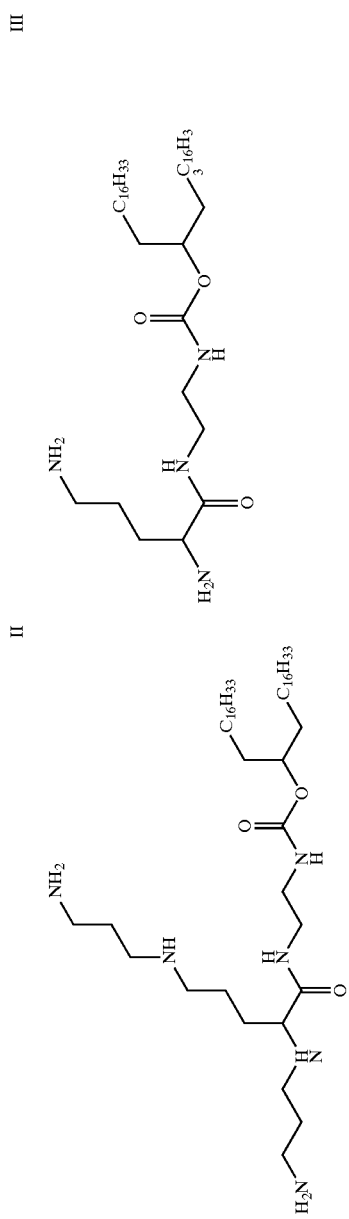
II
III
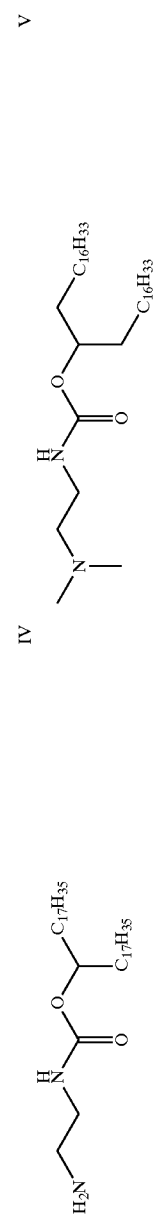
IV
V

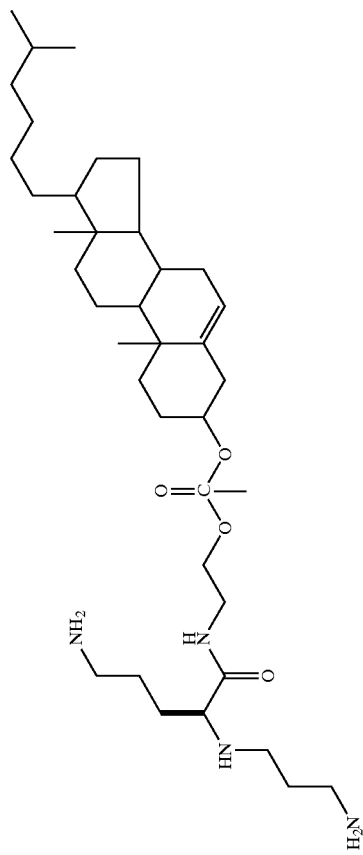
VI
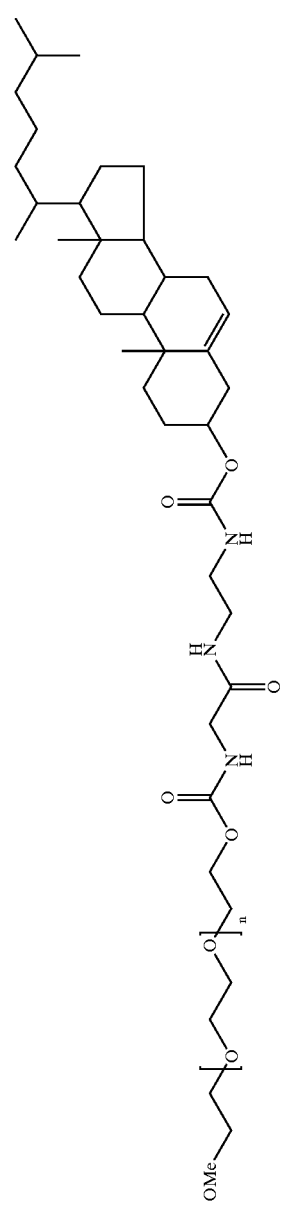
VII
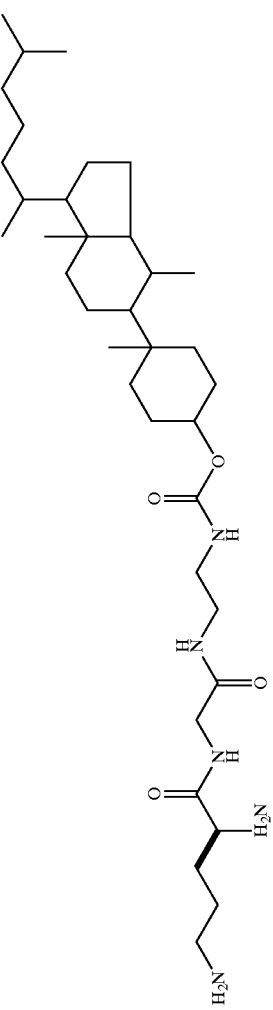
VIII

-continued
IX
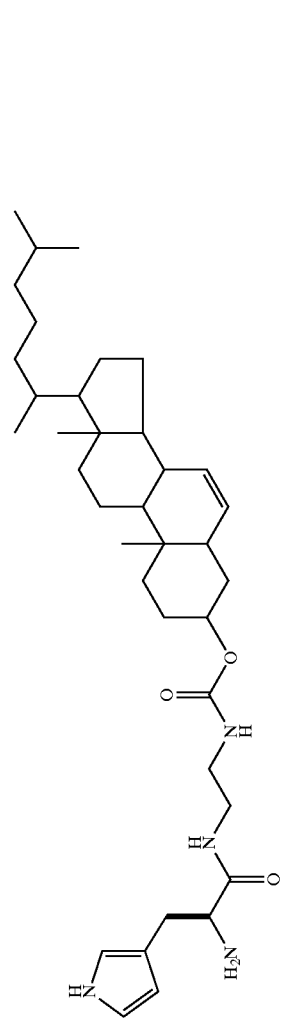
X
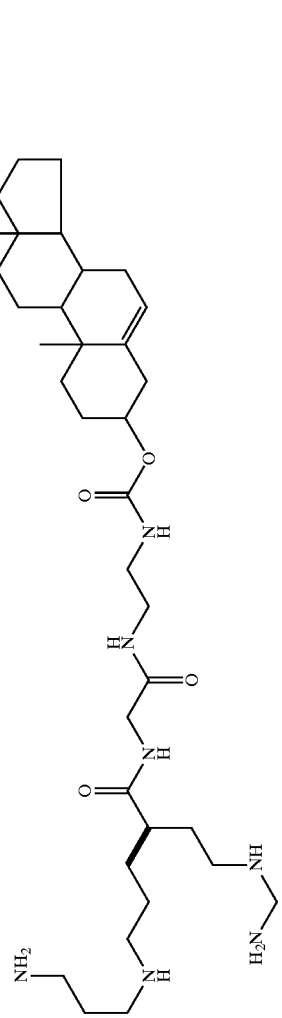
XI
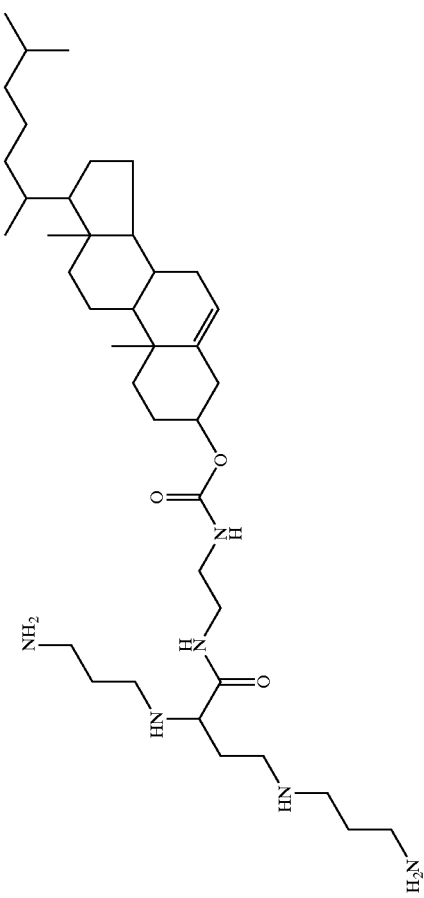

In another aspect of the present invention, compositions comprising a polyanionic macromolecule and any of the lipids described above are provided. In particular, the macromolecule may be a variety of polyanionic macromolecules including an expression vector capable of expressing a polypeptide in a cell, In a prefered the polyanionic macromolecule is an oligomucleotide or an oligomer and most preferably DNA.

In still another aspect of the present invention methods for delivering a polyanionic macromolecule into a cell by contacting any of the compositions above with the cell are provided. In particular, a method is provided to interfere with the expression of a protein in a cell by contacting any of the compositions described above with a cell wherein the composition comprises an oligomer having a base sequence that is substantially complimentary to an RNA sequence in the cell that encodes the protein.

The present invention further provides a kit for delivering a polyanionic macromolecule into a cell comprising any of the compositions described above.

DETAILED DESCRIPTION OF THE INVENTION

Prior to setting forth the remaining description of the invention, it may be helpful to an understanding thereof to first set forth definitions of certain terms that will be used herein after. These terms will have the following meanings unless explicitly stated otherwise:

"Lipophilic Moiety" refers to a moiety which demonstrates one or more of the following characteristics:

| | |
|---|---|
| A. | tend to be water insoluable |
| B. | tend to be soluable in non-polar solvent |
| C. | tend to favor octanol in octanol/water partition measurements, and |
| D. | tend to be compatible with lipid bilayers and may be bilayer forming. |

In particular, lipophilic moieties having an octanol/water partition coefficinet of 0.5 or lower are preferable, where octanol/water partition coefficient is measured by the concentration in water divided by concentration in octanol.

"Positively Charged Moiety" refers to "positively charged moiety and negatively charged moiety" means a moiety, independent of the cationic lipid for which it is a substituent, having a net positive or negative charge within the pH range of 2 to 12. The net charge of the cationic lipid is the summation of all charged moieties occuring on the lipid, such that the net charge may be positive, neutral or negative.

The term "alkyl" refers to saturated aliphatic groups including straight-chain, branched-chain and cyclic groups. Suitable alkyl groups include, but are not limited to, cycloalkyl groups such as cyclohexyl and cyclohexylmethyl. "Lower alkyl" refers to alkyl groups of 1 to 6 carbon atoms. Fluoroalkyl or perfluoroalkyl refers to singly, partially, or fully fluorinated alkyl groups.

The term "alkenyl" refers to an unsaturated aliphatic group having at least one double bond.

The term "arylamine" refers to aromatic groups that have at least one ring having a conjugated pi electron system and includes carbocyclic aryl, heterocyclic aryl and biaryl groups, all of which are substituted with an amine.

The term "aralkylamine" refers to an alkylamine group substituted with an aryl group. Suitable aralkyl groups include benzyl, picolyl, and the like, all of which may be optionally substituted.

The term "heterocyclic amine" refers to groups having from 1 to 3 heteroatoms as ring atoms in the aromatic ring and the remainder of the ring atoms are carbon atoms. Suitable heteroatoms include oxygen, sulfur, and nitrogen, and suitable heterocyclic aryls include furanyl, thienyl, pyridyl, pyrrolyl, pyrimidyl, pyrazinyl, imidazolyl, and the like.

The term "oligonucleoside" or "oligomer" refers to a chain of nucleosides that are linked by internucleoside linkages that is generally from about 4 to about 100 nucleosides in length, but which may be greater than about 100 nucleosides in length. They are usually synthesized from nucleoside monomers, but may also be obtained by enzymatic means. Thus, the term "oligomer" refers to a chain of oligonucleosides that have internucleosidyl linkages linking the nucleoside monomers and, thus, includes oligonucleotides, nonionic oligonucleoside alkyl- and aryl-carbamate analogs, alkyl- and aryl-carbamothioate, analogs of oligonucleotides, carbamate analogs of oligonucleotides, neutral carbamate ester oligonucleoside analogs, other oligonucleoside analogs and modified oligonucleosides, and also includes nucleodeside/non-nucleoside polymers. The term also includes nucleoside/non-nucleoside polymers wherein one or more of the phosphorus group linkage between monomeric units has been replaced by a non-phosphorous linkage such as a formacetal linkage, a thio-formacetal linkage, a morpholino linkage, a sulfamate linkage, a silyl linkage, a carbamate linkage, an amide linkage, a guanidine linkage, a nitroxide linkage or a substituted hydrazine linkage. It also includes nucleoside/non-nucleoside polymers wherein both the sugar and the carbon moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

Lipid Aggregate is a term that includes liposomes of all types both unilamellar and multilamellar as well as micelles and more amorphous aggregates of cationic lipid or lipid mixed with amphipathic lipids such as phospholipids.

Target Cell refers to any cell to which a desired compound is delivered, using a lipid aggregate as carrier for the desired compound.

Transfection is used herein to mean the delivery of expressible nucleic acid to a target cell, such that the target cell is rendered capable of expressing said nucleic acid. It will be understood that the term "nucleic acid" includes both DNA and RNA without regard, to molecular weight, and the term "expression" means any manifestation of the functional presence of the nucleic acid within the cell, including without limitation, both transient expression and stable expression.

Delivery is used to denote a process by which a desired compound is transferred to a target cell such that the desired compound is ultimately located inside the target cell or in, or on the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

The generic structure of functionally active cationic lipids requires three contiguous moities, e.g. cationic-head-group/linker/lipid-tail group. While a wide range of structures can be envisioned for each of the three moieties, it has been demonstrated that there is no a priori means to predict which cationic lipid will successfully transfect anionic macromolecules into a particular cell line. The property of a cationic lipid to be formulated with an anionic macromolecule which will then successfully transfect a cell line is empirical. We demonstrate the abilities of novel cationic lipids which are chemically linked into multimeric constructions to enhance the uptake of macromolecules.

The novel carbamate-based cationic lipids of the present invention have the general structure:

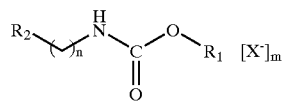

comprising any salt, solvate, or enantiomers thereof. The symbols $R_1$, $R_2$, X, n, and m are described as follows.

$R_1$ represents the lipid-tail group of the carbamate-based cationic lipid and may be a variety of lipophilic moieties, in particular, these include for example, a straight chain alkyl of 1 to about 24 carbon atoms, a straight chain alkenyl of 2 to about 24 carbon atoms, a symmetrical branched alkyl or alkenyl of about 10 to about 50 carbon atoms, a unsymmetrical branched alkyl or alkenyl of about 10 to about 50 carbon atoms, a steroidyl moiety, a glyceryl derivative, a amine derivative, or $OCH(R_4R_5)$ wherein $R_4$ and $R_5$ are straight chain or branched alkyl moieties of about 10 to about 30 carbon atoms.

In the case where $R_1$ is a steriodal moiety a variety of such moieties may be utilized including for example pregnenolone, progesterone, cortisol, corticosterone, aldosterone, androstenedione, testosterone, or cholesterol or analogs thereof. A cholesteryl moiety is particularly preferred.

In particular, $R_1$ may be a 3-(1,2-diacyl)propane 1,2-diol moiety, a 3-(1,2-dialkyl)propane 1,2-diol moiety, a 3-O-1,2-diacylglyceryl moiety, or a 3-O-1,2-dialkylglyceryl moiety. In the case, when $R_1$ is a 3-(1,2-diacyl)propane 1,2-diol moiety or a 3-O-1,2-diacylglyceryl moiety the diacyl group may be an alkanoic acid of about 10 to about 30 carbon atoms or an alkenoic acid of about 10 to about 30 carbon atoms. Similarly, when $R_1$ is a 3-(1,2-dialkyl)propane 1,2-diol moiety or a 3-O-1,2-diacylglyceryl moiety the alkyl moieties may be an alkyl group of about 10 to about 30 carbon atoms or an alkenyl group of about 10 to about 30 carbon atoms. These groups may be straight chain, symmetrically, or unsymmetrically branched alkyl and alkenyl groups.

In either case, when $R_1$ is a propanediol moiety or a glyceryl derivative comprising an alkanoic acid the acid is preferably a stearic acid. Similarly, when these derivative comprise an alkenoic acid the acid is preferably a palmitoic acid or an oleic acid, $R_2$ represents the cationic head group of the carbamate-based cationic lipid and may be a variety of positively charged moieties including, for example, an amino acid residue having a positively charged group on the side chain, an alkylamine moiety of about 3 to about 10 carbon atoms, a fluoroalkylamine moiety or a perfluoroalkylamine moiety of 1 to about 6 carbon atoms; an arylamine moiety or an aralkylamine moiety of about 5 to about 10 carbon atoms, a guanidinium moiety, an enamine moiety, an aromatic or non-aromatic cyclic amine moiety of about 5 to about 10 carbon atoms, an amidine moiety, an isothiourea moiety, a heterocyclic amine moiety, a heterocyclic moiety and an alkyl moiety of 1 to about 6 carbon atoms substituted with a substituent selected from the group consisting of $NH_2$, $C(=O)NH_2$, $NHR_6$, $C(=O)NHR_6$, $NHR_6R_7$ or $C(=O)$ $NHR_6R_7$, wherein $R_6$ and $R_7$, are independently selected from an alkyl moiety of 1 to about 24 carbon atoms, an alkenyl moiety of 2 to about 24 carbon atoms, an aryl moiety of about 5 to about 20 carbon atoms, and an aralkyl moiety of about 6 to about 25 carbon atoms.

In particular when $R_2$ is an amino acid residue it may be, for example, lysine, arginine, histidine, ornithine, or an amino acid analog. Although $R_2$ may be a variety of positively charged amino acid analogs, specific examples include 3-carboxyspermidine, 5-carboxyspermidine, 6-carboxyspermine and a monoalkyl, dialkyl, or peralkyl substituted derivative which is substituted on one or more amine nitrogens with an alkyl group of 1 to about 6 carbon atoms.

The linker comprises the structure joining the head group, $R_1$ to the lipid-tail group, $R_2$. This structure includes Y which may be an oxygen or a nitrogen and a series of —$CH_2$— groups, the number of which, is indicated by the letter n. n is an integer ranging from 1 to 8, in particular cases it ranges from 2 to 6 and in specific instances the integer is 2 to 4.

The counterion represented by $X^-$ is an anion or a polyanion that binds to the positively charged groups present on the carbamic acid-based cationic lipid via charge-charge interactions. When these cationic lipids are to be used in vivo the anion or polyanion should be pharmaceutically acceptable.

m is an integer indicating the number of anions or polyanions associated with the cationic lipid. In particular this integer ranges in magnitude from 0 to a number equivalent to the positive charge(s) present on the lipid.

The cationic lipids of the present invention include salts, solvates, or enantiomeric isomers resulting from any or all asymmetric atoms present in the lipid. Included in the scope of the invention are racemic mixtures, diastereomeric mixtures, optical isomers or synthetic optical isomers which are isolated or substantially free of their enantiomeric or diasteriomeric partners. The racemic mixtures may be separated into their individual, substantially optically pure isomers by techniques known in the art, such as, for example, the separation of diastereomeric salts formed with optically active acid or base adjuncts followed by conversion back to the optically active substances. In most instances, the desired optical isomer is synthesized by means of stereospecific reactions, beginning with the appropriate stereoisomer of the desired starting material. Methods and theories used to obtain enriched and resolved isomers have been described (Jacques et al., "Enantiomers, Racemates and Resolutions." Kreiger, Malabar, Fla., 1991).

The salts include pharmaceutically or physiologically acceptable non-toxic salts of these compounds. Such salts may include those derived by combination of appropriate cations such as alkali and alkaline earth metal ions or ammonium and quaternary amino ions with the acid anion moiety of the carbamate or carbamothioate acid group present in polynucleotides. Suitable salts include for example, acid addition salts such as HCl, HBr, HF, HI, $H_2SO_4$, and trifluoroacetate. The salts may be formed from acid addition of certain organic and inorganic acids, e.g., HCl, Hbr, $H_2SO_4$, amino acids or organic sulfonic acids, with basic centers, (e.g. amines), or with acidic groups. The composition herein also comprise compounds of the invention in their un-ionized, as well as zwitterionic forms.

Exemplary invention cationic lipids have the structures shown in the Summary of the Invention above.

The cationic lipids form aggregates with polyanionic macromolecules such as oligonucleotides, oligomers, peptides, or polypeptides through attraction between the positively charged lipid and the negatively charged polyanionic macromolecule. The aggregates may comprise multiamellar or unilamellar liposomes or other particles. Hydrophobic interactions between the cationic lipids and the hydrophobic substituents in the polyanionic macromolecule such as aromatic and alkyl moieties may also facilitate aggregate formation. Cationic lipids have been shown to efficiently deliver nucleic acids and peptides into cells in the presence of serum and thus are suitable for use in vivo or ex vivo.

Cationic lipid-polyanionic macromolecule aggregates may be formed by a variety of method known in the art. Representative methods are disclosed by Felgner et al., supra; Eppstein et al. supra; Behr et al. supra; Bangham, A. et al. *M. Mol. Biol.* 23:238, 1965; Olson, F. et al. *Biochim. Biophys. Acta* 557:9, 1979; Szoka, P. et al. *Proc. Natl. Acad. Sci.* 75: 4194, 1978; Mayhew, E. et al. *Biochim. Biophys. Acta* 775:169, 1984; Kim, S. et al. *Biochim. Biophys. Acta* 728:339, 1983; and Fukunaga, M. et al. *Endocrinol.* 115:757, 1984. Commonly used techniques for preparing lipid aggregates of appropriate size for use as delivery vehicles include sonication and freeze-thaw plus extrusion. See, e.g., Mayer, L. et al. *Biochim. Biophys. Acta* 858:161, 1986. Microfluidization is used when consistently small (50 to 200 nm) and relatively uniform aggregates are desired (Mayhew, E., supra). In general aggregates may be formed by preparing lipid particles consisting of either (1) a cationic lipid of the invention or (2) a cationic lipid mixed with a colipid, followed by adding a polyanionic macromolecule to the lipid particles at about room temperature (about 18 to 26° C.). In general, conditions are chosen that are not conducive to deprotection of protected groups. The mixture is then allowed to form an aggregate over a period of about 10 minutes to about 20 hours, with about 15 to 60 minutes most conveniently used. The complexes may be formed over a longer period, but additional enhancement of transfection efficiency will not usually be gained by a longer period of complexing. Colipids that are suitable for preparing lipid aggregates with the cationic lipids of the present invention are dimyristoylphosphatidylethanolamine, dipalmitoylphosphatidylethanolamine, palmitoyloleolphosphatidylethanolamine, cholesterol, distearoylphosphatidylethanolamine, phosphatidylethanolamine covalently linked to polyethylene glycol and mixtures of these colipids.

The optimal cationic lipid:colipid ratios for a given cationic lipid is determined by mixing experiments to prepare lipid mixtures for aggregation with a polyanionic macromolecule using cationic lipid:colipid ratios between about 1:0 and 1:10. Methods to determine optimal cationic lipid-:colipid ratios have been described (see, Felgner, infra). Each lipid mixture is optionally tested using more than one oligonucleotide-lipid mixture having different nucleic acid:lipid molar ratios to optimize the oligonucleotide:lipid ratio.

Suitable molar ratios of cationic lipid:colipid are about 0.1:1 to 1:0.1, 0.2:1 to 1:0.2, 0.4:1 to 1:0.4, or 0.6:1 to 1:0.6. Lipid particle preparation containing increasing molar proportions of colipid have been found to enhance oligonucleotide transfection into cells with increasing colipid concentrations.

In addition, the cationic lipids can be used together in admixture, or different concentrations of two or more cationic lipids in admixture, with or without, colipid.

Liposomes or aggregates are conveniently prepared by first drying the lipids in solvent (such as chloroform) under reduced pressure. The lipids are then hydrated and converted to liposomes or aggregates by adding water or low ionic strength buffer (usually less than about 200 mM total ion concentration) followed by agitating (such as vortexing and/or sonication) and/or freeze/thaw treatments. The size of the aggregates or liposomes formed range from about 40 nm to 600 nm in diameter.

The amount of an oligonucleotide delivered to a representative cell by at least some of the cationic lipids was found to be significantly greater than the amount delivered by commercially available transfection lipids. The amount of oligonucleotide delivered into cells was estimated to be about 2- to 100-fold greater for these cationic lipids of the invention based on the observed fluorescence intensity of transfected cells after transfection using a fluorescently labeled oligonucleotide. The cationic lipids described herein also transfect some cell types that are not detectably transfected by commercial lipids. Functionality of cationic lipid-DNA aggregates was demonstrated by assaying for the gene product of the exogenous DNA. Similarly the functionality of cationic lipid-oligonucleotide aggregates were demonstrated by antisense inhibition of a gene product.

The cationic lipids described herein also differed from commercially available lipids by efficiently delivering an oligonucleotide into cells in tissue culture over a range of cell confluency from about 50 to 100%. Most commercially available lipids require cells that are at a relatively narrow confluency range for optimal transfection efficiency. For example, Lipofectin™ requires cells that are 70–80% confluent for transfecting the highest proportion of cells in a population. The cationic lipids described herein may be used to transfect cells that are about 10–50% confluent, but toxicity of the lipids was more pronounced, relative to that seen using cells that are about 50–100% confluent. In general, the cationic lipids transfected cells that were about 60–100% confluent with minimal toxicity and optimal efficiency. Confluency ranges of 60–95% or 60–90% are thus convenient for transfection protocols with most cell lines in tissue culture.

The cationic lipid aggregates were used to transfect cells in tissue culture and the RNA and the DNA encoded gene products were expressed in the transfected cells.

The cationic lipid aggregates may be formed with a variety of macromolecules such as oligonucleotides and oligomers. Oligonucleotides used in aggregate formation may be single stranded or double stranded DNA or RNA, oligonucleotide analogs, and plasmids.

In general, relatively large oligonucleotides such as plasmids or mRNAs will carry one or more genes that are to be expressed in a transfected cell, while comparatively small oligonucleotides will comprise (1) a base sequence that is complementary (via Watson Crick or Hoogsteen binding) to a DNA or RNA sequence present in the cell or (2) a base sequence that permits oligonucleotide binding to a molecule inside a cell such as a peptide, protein or glycoprotein. Exemplary RNAs include ribozymes and antisense RNA sequences that are complementary to a target RNA sequence in a cell An Oligonucleotide may be a single stranded unmodified DNA or RNA comprising (a) the purine or pyrimidine bases guanine, adenine, cytosine, thymine and/or uracil: (b) ribose or deoxyribose; and (c) a phosphodiester group that linkage adjacent nucleoside moieties. Oligonucleotides typically comprise 2 to about 100 linked nucleosides. Typical oligonucleotides range in size from 2–10, 2–15, 2–20, 2–25, 2–30, 2–50, 8–20, 8–30 or 2–100 linked nucleotides. Oligonucleotides are usually linear with uniform polarity and, when regions of inverted polarity are present, such regions comprise no more than one polarity inversion per 10 nucleotides. One inversion per 20 nucleotides is typical. Oligonucleotides can also be circular, branched or double-stranded. Antisense oligonucleotides generally will comprise a sequence of about from 8–30 bases or about 8–50 bases that is substantially complementary to a DNA or RNA base sequence present in the cell. The size of oligonucleotide that is delivered into a cell is limited only by the size of polyanionic macromolecules that can reasonably be prepared and thus DNA or RNA that is 0.1 to 1 Kilobase (Kb), 1 to 20 Kb, 20 Kb to 40 Kb or 40 Kb to 1,000 Kb in length may be delivered into cells.

Oligonucleotides also include DNA or RNA comprising one or More covalent modifications. Covalent modifications include (a) substitution of an oxygen atom in the phosphodiester linkage of an polynucleotide with a sulfur atom, a methyl group or the like, (b) replacement of the phosphodiester group with a nonphosphorus moiety such as —O—CH$_2$O—, S—CH$_2$O— or O CH$_2$O—S, and (c) replacement of the phosphodiester group with a phosphate analog such as —O—P(S)(O)—O—, —O—P(S)(S)—O—, —O—P(CH$_3$)(O)—O or —O—P(NHR$^{10}$)(O)—O— where R$^{10}$ is alkyl (C$_{1-6}$), or an alkyl ether (C$^{1-6}$). Such substitutions may constitute from about 10% to 100% or about 20 to about 80% of the phosphodiester groups in unmodified DNA or RNA. Other modifications include substitutions of or on sugar moiety such as morpholino, arabinose 2'-fluororibose, 2'-fluoroarabinose, 2'—O—methylribose or 2'-O-allylribose. Oligonucleotides and methods to synthesize them have been described (for example see: U.S. patent application Ser. Nos. 08/154,013, filed Nov. 16, 1993, 08/154,014, filed Nov. 16, 1993, 08/001,179, filed Jun. 6, 1993, and 08/233,778 filed May 4, 1994, PCT/US90/03138, PCT/US90/06128, PCT/US90/06090, PCT/US90/06110, PCT/US92/03385, PCT/US91/08811, PCT/US91/03680, PCT/US91/06855, PCT/US91/01141, PCT/US92/10115, PCT/US92/10793, PCT/US93/05110, PCT/US93/05202, PCT/US92/04294, WO 86/05518, WO 89/12060, WO 91/08213, WO 90/15065, WO 91/15500, WO 92/02258, WO 92/20702, WO 92/20822, WO 92/20823, U.S. Pat. No. : 5,214,136 and Uhlmann *Chem Rev.* 90:543, 1990). Oligonucleotides are usually linear with uniform polarity and, when regions of inverted polarity are present, such regions comprise. no more than one polarity inversion per 10 nucleotides, One inversion per 20 nucleotides is typical. Oligonucleotides may also be circular, branched or double-stranded.

The linkage between the nucleotides of the oligonucleotide may be a variety of moieties including both phosphorus-containing moieties and non phosphorus-containing moieties such as formacetal, thioformacetal, riboacetal and the like. A linkage usually comprises 2 or 3 atoms between the 5' position of a nucleotide and the 2' or 3' position of an adjacent nucleotide. However, other synthetic linkers may contain greater than 3 atoms.

The bases contained in the oligonucleotide may be unmodified or modified or natural or unatural purine or pyrimidine bases and may be in the α or β anomer. Such bases may be selected to enhance the affinity of oligonucleotide binding to its complementary sequence relative to bases found in native DNA or RNA. However, it is preferable that modified bases are not incorporated into an oligonucleotide to an extent that it is unable to bind to complementary sequences to produce a detectably stable duplex or triplex.

Exemplary bases include adenine, cytosine, guanine, hypoxanthine, inosine, thymine, uracil, xanthine, 2-aminopurine, 2,6-diaminopurine, 5-(4-methylthiazol-2-yl) uracil, 5-(5-methylthiazol-2-yl)uracil, 5-(4-methylthiazol-2-yl)cytosine, 5-(5-methylthiazol-2-yl)cytosine and the like. Other exemplary bases include alkylated or alkynylated bases having substitutions at, for example, the 5 position of pyrimidines that results in a pyrimidine base other than uracil, thymine or cytosine, (i.e., 5-methylcytosine, 5-(1-propynyl)cytosine, 5-(1-butynyl)cytosine, 5-(1-butynyl) uracil, 5-(1-propynyl)uracil and the like). The use of modified bases or base analogs in oligonucleotides have been previously described (see PCT/US92/10115; PCT/US91/08811; PCT/US92/09195; WO 92/09705; WO 92/02258; Nikiforov, et al., *Tet. Lett.* 33:2379, 1992; Clivio, et al., *Tet. Lett.* 33:65, 1992; Nikiforov, et al., *Tet. Lett.* 32:2505, 1991; Xu, et al., *Tet. Lett.* 32:2817, 1991; Clivio, et al., *Tet. Lett.* 33:69, 1992; Connolly, et al., *Nucl. Acids Res.* 17:4957, 1989).

Aggregates may comprise oligonucleotides or oligomers encoding a therapeutic or diagnostic polypeptide. Examples of such polypeptides include histocompatibility antigens, cell adhesion molecules, cytokines, antibodies, antibody fragments, cell receptor subunits, cell receptors, intracellular enzymes and extracellular enzymes or a fragment of any of these. The oligonucleotides also may optionally comprise expression control sequences and generally will comprise a transcriptional unit comprising a transcriptional promoter, an enhancer, a transcriptional terminator, an operator or other expression control sequences.

Oligonucleotides used to form aggregates for transfecting a cell may be present as more than one expression vector. Thus, 1, 2, or 3 or more different expression vectors may be delivered into a cell as desired. Expression vectors will typically express 1, 2, or 3 genes when transfected into a cell, although many genes may be present such as when a herpes virus vector or a yeast artificial chromosome is delivered into a cell. Expression vectors that are introduced into a cell can encode selectable markers (e.g. neomycin phosphotransferase, thymidine kinase, xanthine-guanine phosphoribosyl-transferase, and the like) or biologically active proteins such as metabolic enzymes or functional proteins (e.g. immunoglobulin genes, cell receptor genes, cytokines (e.g. IL-2, IL-4, GM-CSF, γ-INF and the like), or genes that encode enzymes that mediate purine or pyrimidine metabolism and the like).

The nucleic acid sequence of the oligonulcleotide coding for specific genes of interest may be retrieved, without undue experimentation, from the GenBank of EMBL DNA libraries. Such sequences may include coding sequences, for example, the coding sequences for structural proteins, hormones, receptors and the like, and the DNA sequences for other DNAs of interest, for example, transcriptional and translational regulatory elements (promoters, enhancers, terminators, signal sequences and the like), vectors (integrating or autonomous) and the like. Non-limiting examples of DNA sequences which may be introduced into cells with the reagent of the invention include those sequences coding for fibroblast growth factor (see WO 87/01728); ciliary neurotrophic factor (Lin et al., *Science,* 246:1023, 1989; human interferon-α receptor (Uze, et al., *Cell,* 60:225,,1990; the interleukins and their receptors (reviewed in Mizal, *FASEB J.,* 3:2379, 1989; hybrid interferons (see EPO 051,873); the RNA genome of human rhinovirus (Callahan, *Proc. Natl. Acad. Sci.*, 82:732, 1985; antibodies including chimeric antibodies (see U.S. Pat. No.: 4,816,567); reverse transcriptase (see Moelling, et al., *J. Virol.*, 32:370, 1979; human CD4 and soluble forms thereof (Maddon et al., *Cell*, 47:333, 1986, see WO 88/01304 and WO 89/01940); and EPO 330,191, which discloses a rapid immunoselection cloning method useful for the cloning of a large number of desired proteins.

Aggregates can be used in antisense inhibition of gene expression in a cell by delivering an antisense oligonucleotide into the cell (see Wagner, *Science* 260:1510, 1993 and WO 93/10820). Such oligonucleotides will generally comprise a base sequence that is complementary to a target RNA sequence that is expressed by the cell. However, the oligonucleotide may regulate intracellular gene expression by binding to an intracellular nucleic acid binding protein (see Clusel, *Nucl. Acids Res.* 21:3405, 1993) or by binding to an intracellular protein or organelle that is not known to bind to nucleic acids (see WO 92/14843). A cell that is blocked for expression of a specific gene(s) is useful for manufacturing and therapeutic applications. Exemplary manufacturing uses include inhibiting protease synthesis in a cell to increase production of a protein for a therapeutic or diagnostic application (e.g., reduce target protein degradation caused by the protease). Exemplary therapeutic applications include inhibiting synthesis of cell surface antigens to reduce rejection and/or to induce immunologic tolerance of the cell either after it is implanted into a subject or when the cell is transfected in vivo (e.g. histocompatibility antigens, such as MHC class II genes, and the like).

Methods to introduce aggregates into cells in vitro and in vivo have been previously described (see U.S. Pat. Nos.: 5,283,185 and 5,171,678; WO 94/00569; WO 93/24640; WO 91/16024; Felgner, *J. Biol Chem* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J*. 11:417, 1992.

Entry of liposomes or aggregates into cells may be by endocytosis or by fusion of the liposome or aggregate with the cell membrane. When fusion takes place, the liposomal membrane is integrated into the cell membrane and the aqueous contents of the liposome merge with the fluid in the cell.

Endocytosis of liposomes occurs in a limited class of cells; those that are phagocytic, or able to ingest foreign particles. When phagocytic cells take up liposomes or aggregates, the cells move the spheres into subcellular organelles known as lysosomes, where the liposomal membranes are thought to be degraded. From the lysosome, the liposomal lipid components probably migrate outward to become part of cell's membranes and other liposomal components that resist lysosomal degradation (such as modified oligonucleotides or oligomers) may enter the cytoplasm.

Lipid fusion involves the transfer of individual lipid molecules from the liposome or aggregate into the plasma membrane (and vice versa); the aqueous contents of the liposome may then enter the cell. For lipid exchange to take place, the liposomal lipid must have a particular chemistry in relation to the target call. Once a liposomal lipid joins the cell membrane it can either remain in the membrane for a period of time or be redistributed to a variety of intracellular membranes. The invention lipids can be used to deliver an expression vector into a cell for manufacturing or therapeutic use. The expression vectors can be used in gene therapy protocols to deliver a therapeutically useful protein to a cell or for delivering nucleic acids encoding molecules that encode therapeutically useful proteins or proteins that can generate an immune response in a host for vaccine or other immunomodulatory purposes according to known methods (see U.S. Pat. Nos.: 5,399,346 and 5,336,615, WO 94/21807 and WO 94/12629). The vector-transformed cell can be used to produce commercially useful cell lines, such as a cell line for producing therapeutic proteins or enzymes (e.g. erythropoietin, and the like), growth factors (e.g. human growth hormone, and the like) or other proteins. The aggregates may be utilized to develop cell lines for gene therapy applications in humans or other species including murine, feline, bovine, equine, ovine or non-human primate species. The aggregates may be used in the presence of serum and will thus deliver polyanionic macromolecules into cells in tissue culture medium containing serum in vitro or in an animal in vivo.

The following examples are offered by way of illustration and not by way of limitation.

DESCRIPTION OF THE FIGURES

FIG. 6 Compares nuclear delivery of varying-charge-density oligonucleotides using novel cationic lipids versus commercially available lipids in COS-7 Cells, SNB 19 Cells, HeLa Cells, and HT1080 cells.

EXAMPLES

General Methods

Figure 1:
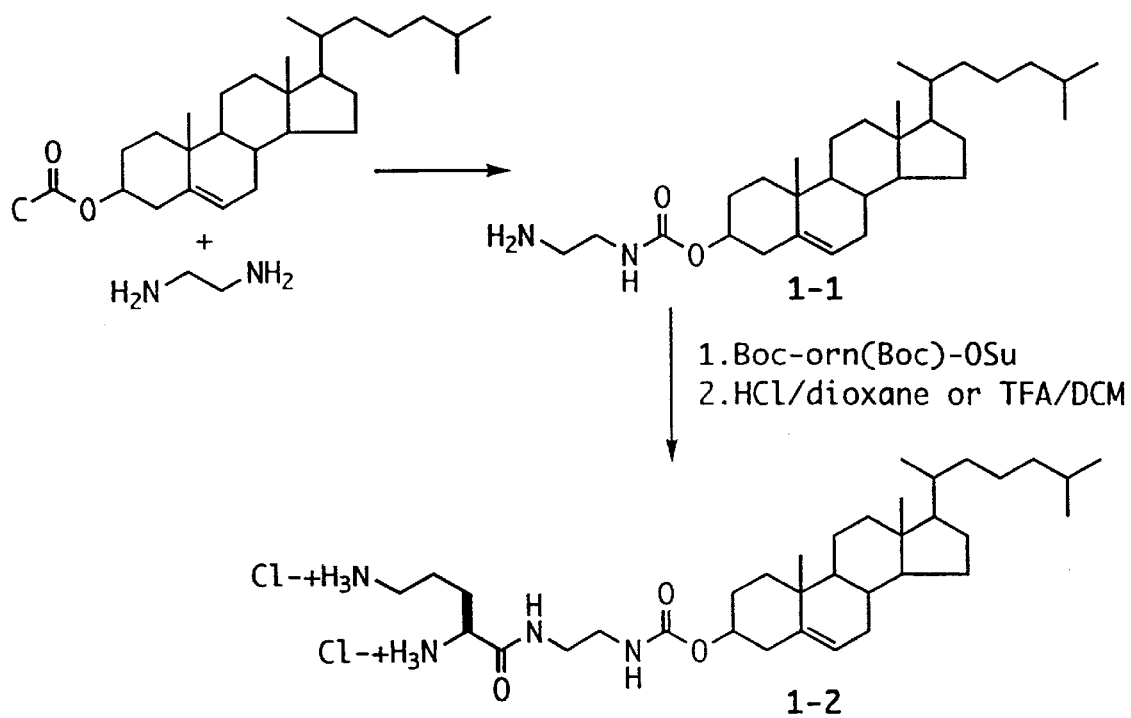
FIG. 1 depicts synthetic route for the synthesis of 1-2.
Figure 2:
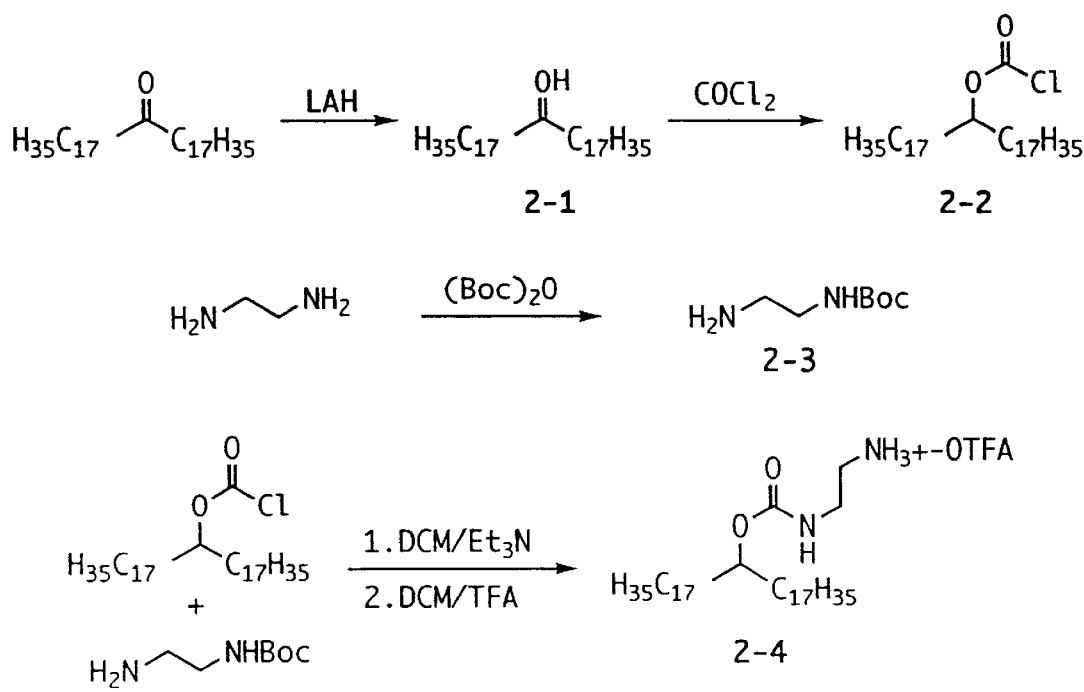
FIG. 2 depicts synthetic route for the synthesis of 2-4.
Figure 3:
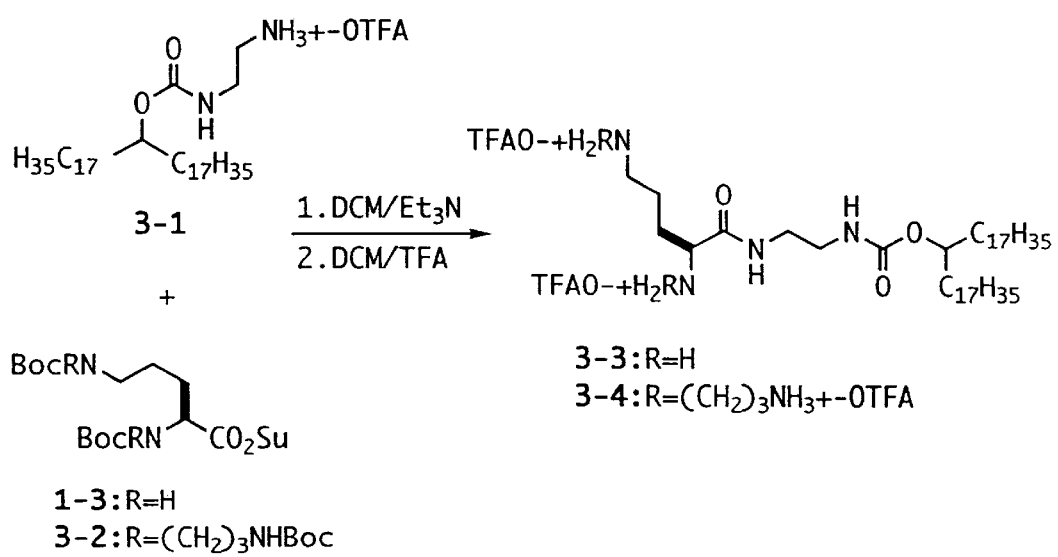
FIG. 3 depicts synthetic route for the syntheses of 3-3 and 3-4.
Figure 4:
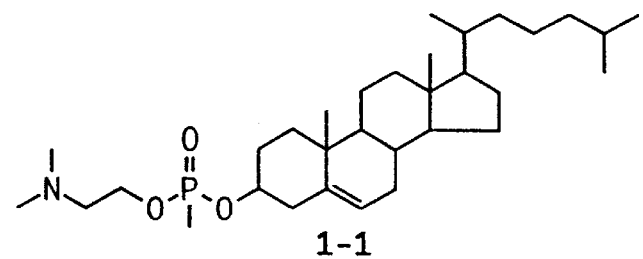
FIG. 4 depicts structure of 4-1 (3β-cholest-5-en-3-ol, 2-(dimethylamino)ethyl methyl phosphonate), 4-2 (3β-cholest-5-en-3-ol, 2-((2,5-diamino-1-oxopentyl)amino) ethyl methyl phosphonate, dihydrochloride), and 4-3(N-α-(6-carboxyspermino)-N, N-dioctadecylglutamic acid-γ-amide, tetra(trifluoroacetate)). The syntheses of 4-1, 4-2, and 4-3 are described in the commonly assigned and concurrently filed U.S. Patent Application "Novel Methylphosphonate Cationic Lipids".
Figure 4:
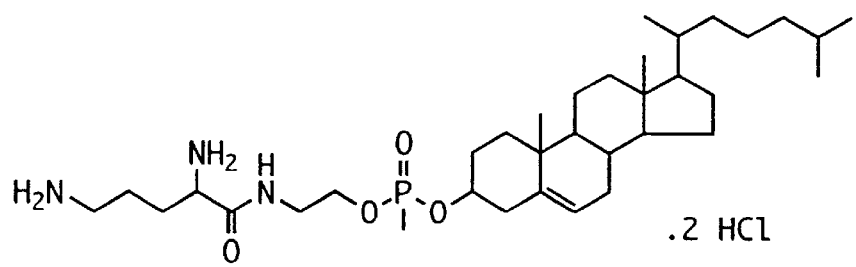
Figure 4:
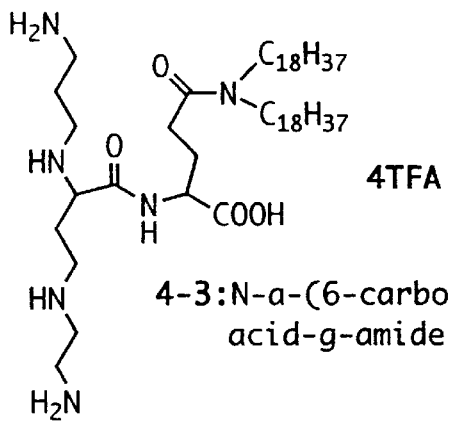
Figure 5:
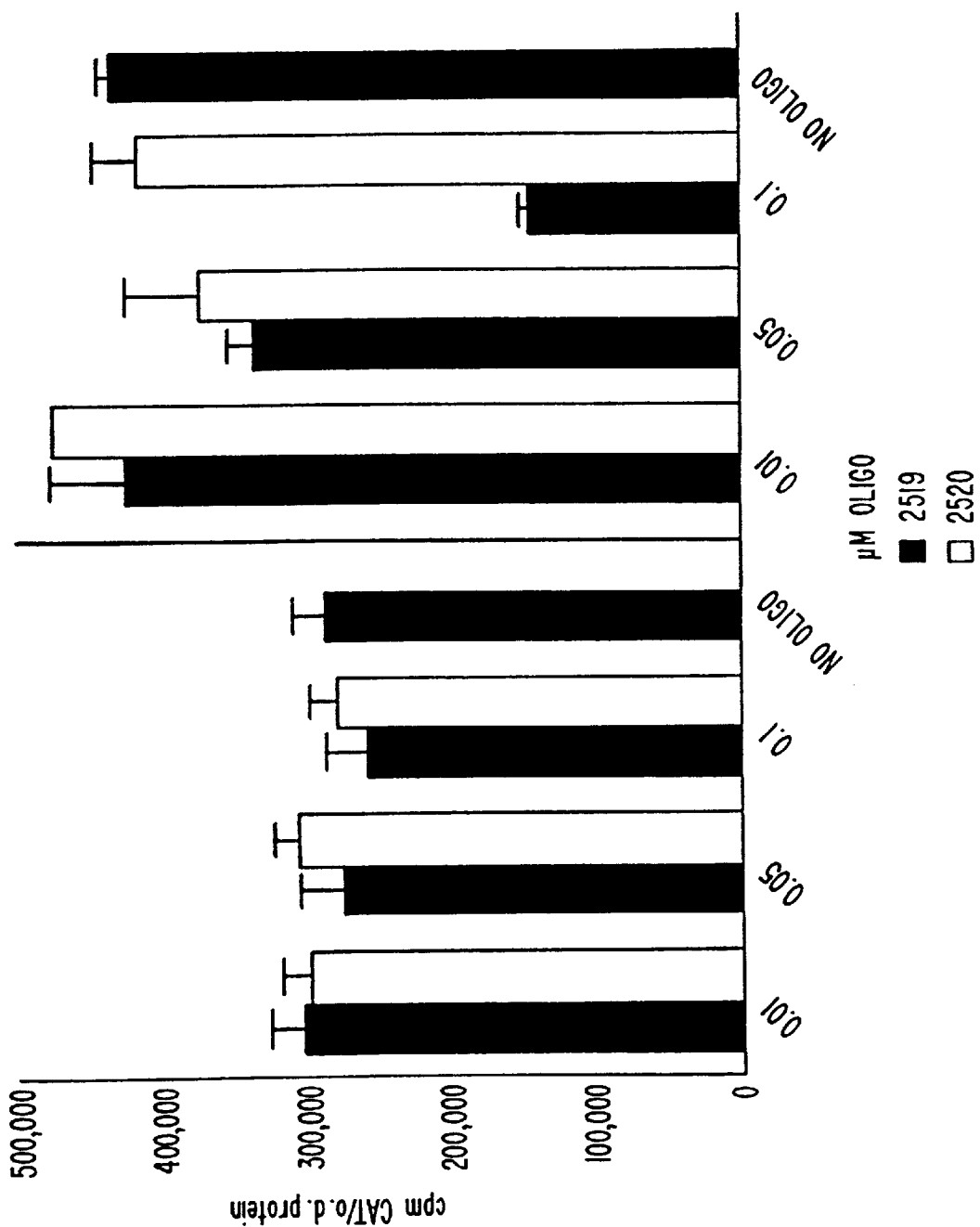
FIG. 5 depicts the combination of cationic lipids 1-2/44-1 delivers plasmids and oligodeoxynucleotides into cells as demonstrated by the dose dependent protein translation arrest.

All reactions were run under a positive pressure of dry argon. Reactions requiring anhydrous conditions were performed in flame-dried glassware which was cooled under argon. Tetrahydrofuran (THF, Aldrich Milwaukee, Wis.) was distilled from potassium/benzophenone ketyl immediately prior to use. Methylene chloride, pyridine, toluene, heptane, methanol, and ethanol were obtained as anhydrous reagent (<0.005% water) or reagent grade and were used without further purification. TLC was performed on 0.2 mm E. Merck precoated silica gel 60 $F_{254}$ TLC plates (20×20 cm aluminum sheets, Fisher, Pa.). Flash chromatography was performed using E. Merck 230–400 mesh silica gel. All $^1$H, $^{13}$C and $^{31}$P NMR spectra were recorded on a 300 MHz Bruker ARX Spectrometer (Bruker, Boston, Mass.) and were obtained in $CDCl_3$ unless otherwise indicated. Mass spectra were provided by The Scripps Research Institute Mass Spectrometry Facility of La Jolla, Calif. FAD mass spectra were obtained on a FISONS VG ZAB-VSE double focussing mass spectrometer (Fisons, Altrincham UK) equipped with a cesium ion gun. ESI mass spectra were obtained on an API III PE Sciex triple-quadrupole mass spectrometer (Sciex, Toronto Calif.).

Example 1

Synthesis of Cholest-5-en-3-ol(3β)-, [2-[2,3-diamino-1-oxopentyl)amino]ethyl]carbamate, Dihydrochloride (1-2)

N-Cholesteryloxycarbonylethylenediamine (1—1) was prepared as follows and used without further purification. A solution of cholesteryl chloroformate (20 mmol) in dichloromethane (50 mL) was added dropwise to a cooled (ice-water bath) solution of ethylenediamine (400 mmol) in dichloromethane (200 mL). After 3 hours the solvent was evaporated, and the residue was recrystallized from ethanol (50% yield). The dimer (N,N'-dicholesteryloxycarbonyl-ethylenediamine) is insoluble in hot ethanol and was filtered away. $^1$H NMR (300 MHz, CDCl$_3$, TMS=0), δ5.37 (d, 1H, J=5.2), 4.9 (m, 1H), 4.51 (m, 1H), 3.21 (dd, 2H, J=5.8, 11.7), 2.81 (t, 2H, J=5.8), 2.41–2.20 (m, 2H), 2.05–1.75 (m, 5H), 1.63–0.92 (m, 24H), 1.01 (s, 3H), 0.91 (d, 3H, J=6.5), 0.86 (d, 6H, J=6.6), 0.68 (s, 3H).

Na-Nd-Bis-t-butyloxycarbonyl-L-ornithine succinimidyl ester (Boc-orn(Boc)-OSu) (1–3) was prepared as follows and used without further purification. To a solution of Na-Nd-bis-t-butyloxycarbonyk-L-ornithine (4.98 g, (15 mmol)) in dioxane (100 mL) was added N-hydroxysuccinimide (1.9 g, (16.5)) followed by dicyclohexylcarbodiimide (3.56 g, (16.5 mmol)). The reaction mixture was stirred overnight at room temperature. After removing the dicyclohexylurea by filtration the solvent was removed, and the resulting residue was dissolved in ethyl acetate (75 mL). The organic layer was washed with 5% sodium bicarbonate, water, then dried with anhydrous sodium sulfate. The solvent was evaporated to afford a white solid (4.76 g, 74% yield).

To a solution of 1–3 (4.4 mmol) in dichloromethane/dioxane, 1:1 (50 mL) was added 1—1 (4.4 mmol). The reaction proceeded at room temperature for 18 hours. The product was purified by chromatography on silica gel (5% methanol in dichloromethane). Obtained 1.5 g; 49%. The product was deprotected using HCl/dioxane for 1 hour. $^1$H NMR (300 MHz, CDCl$_3$+CD$_3$OD, TMS=0), δ5.37 (d, 1H, J=4.0), 4.42 (m, 1H), 3.93 (m, 1H), 3.36–3.30 (m, 4H), 2.98 (t, 2H, J=7.2), 2.33 (m, 2H), 2.10–0.80 (m, 46H), 0.70 (s, 3H); FABMS m/z (M$^+$) calcd for C$_{35}$H$_{62}$N$_4$O$_3$ 587, found 588 (M+1)$^+$.

Example 2

Synthesis of N-(18-Pentatricontyloxycarbonyl)-2-aminoethanol Trifluoroacetate (2—4)

18-Hydroxypentatriacontane (2-1) was prepared as follows and used without further purification. In a dry flask charged with argon was prepared a solution of lithium aluminum hydride (0.75 g, (19.8 mmol)) in freshly distilled tetrahydrofuran (400 mL). To this solution was added stearone (5.0 g, (9.9 mmol)). The reaction mixture was slowly brought to reflux (and allowed to stir at reflux overnight). After cooling to room temperature, the remaining lithium aluminum hydride was quenched by the dropwise addition of water (0.76 mL), followed by 15% NaOH (0.76 mL), and water again (2.2 mL). The reaction mixture was allowed to stir for 1 hour. The solvent was evaporated, and the resulting solids were triturated with hot toluene (300 mL). The toluene was evaporated to yield the desired alcohol (4.9 g. 97% yield) $^1$H NMR (300 MHz, CDCl$_3$, TMS=0), δ3.58 (m, 1H), 1.38 (m, 4H), 1.25 (bs, 60H), 0.88 (t, 6H, J=6.5).

(18-Pentatricontyl)chloroformate (2—2) was prepared as follows and used without further purification. In a dry flask charged with argon was prepared a solution of 2-1 (2 g, (3.9 mmol)) in freshly distilled tetrahydrofuran. To this was added triphosgene (1.28 g, (3.9 mmol)), followed by a catalytic amount of activated carbon. A condenser and a trap flask containing methanol was used. The reaction was allowed to stir at reflux for 2 hours, and while still warm, the reaction mixture was filtered through Celite. Argon was bubbled through the reaction mixture to remove any phosgene and HCl that was still present. The solution containing the desired product used in the next step without purification.

N-t-Butyloxycarbonylethylenediamine (2-3) was prepared as follows and used without further purification. To a round bottom flask was added ethylenediamine (61.4 mL, (920 mmol)) was allowed to equilibrate to -5° C. A solution of di-t-butyl-dicarbonate (10 g, (46 mmol)) in dichloromethane (150 mL) was then added dropwise. Once addition was complete, more dichloromethane was added (200 mL). After stirring for 15 minutes at -5° C., water was added (125 mL). The organic layer was washed with water (3×75 mL), and dried with anhydrous sodium sulfate. The solvent was evaporated to afford (5.0 g, 68% yield) of a slightly colored oil.

To a solution of 2—2 (2.24 g, (3.9 mmol)) in dichloromethane (350 mL) was added triethylamine (3.3 mL, 23.4 mmol) followed by a solution of 2-3 (0.94 g, (5.9 mmol)) in anhydrous tetratydrofuran (7 mL). The reaction mixture stirred at reflux for 1 hour, and the insoluble material was filtered away. The crude product (2.9 g), was purified by flash chromatography on silica gel (heptane, ethyl acetate, 4:1; Rf=0.18). A white solid was obtained (1.4 g, 52% yield). The purified product (0.2 g, (0.3 mmol)) was then deprotected with trifluoroacetic acid/dichloromethane 1:1 (2 mL,) for 20 minutes. After coevaporation with 1,2-dichloroethane the desired product 2-4 was obtained (175 mg, 87% yield)

Example 3

Synthesis of Carbamic Acid, [2-[(2,5-diamino-1-oxopentyl)amino]ethyl]-1-heptadoecyloctadecyl ester, Dihydrochloride, Dihydrochloride, (S)$^-$ (3-4)

Carbamic acid, [2-[(2,5-diamino-1-oxopentyl)amino]ethyl]-1-heptadoecyloctadecyl ester, dihydrochloride, dihydrochloride, (S)$^-$(3—3). A solution was prepared of 3-1(0.190 g, (0.44 mmol)) in anhydrous methylene chloride (5 mL). To this solution was added dropwise a solution of 1-3 in anhydrous methylene chloride (5 mL) followed by triethylamine (0.154 mL, (1.1 mmol)). The reaction mixture was heated to reflux for 10 minutes. The reaction mixture was cooled to room temperature, washed with water (2×2 mL), and dried with anhydrous sodium sulfate. The product was obtained by flash chromatography on silica gel (0.374 g, 94%). The purified product was then deprotected with trifluoroacetic acid/dichloromethane 1:1 (30 mL) for 20 minutes. After coevaporation from 1,2-dichloroethane, the desired product 3—3 was obtained (0.362 g, 94% yield). $^1$H NMR (300 MHz, CDCl$_3$+CD$_3$OD, TMS=0), δ3.77 (m, 1H), 3.31 (m, 2H), 2.97 (t, 2H, J=6.5), 2.00–1.65 (m, 6H), 1.65–1.31 (m, 4H), 1.29 (bs, 60H), 0.91 (t, 6H, J=7.0); ESIMS m/z (M$^+$) calcd for C$_{43}$H$_{88}$N$_4$O$_3$ 709, found 710 (M+1)$^+$.

Example 4

Synthesis of Carboxyspermyl-N-(18-pentatriacontyloxycarbonyl)ethylenediamine (3–4)

N,N$^2$,N$^3$,N$^4$-Tetrakis-(tert-butoxycarbonyl)spermine-carboxylic acid N-hydroxysuccinimydyl ester (3-2) was prepared as follows and used without further purification. A 100-mL round-bottomed reaction flask was charged with $N,N^2,N^3,N^4$-Tetrakis-(tert-butoxycarbonyl)spermine-5-carboxylic acid (Behr, J. P. Acc. Chem. Res. 26, 274, 1993) (2.08 g, (3.2 mmol)), dicyclohexylcarbodiimide (0.73 g, (3.5 mmol)), 1-hydroxybenzotriazole hydrate (0.41 g, (3.5 mmol)), and methylene chloride (20 mL). The reaction mixture was stirred for 5 hours and then placed in a refrigerator (0–5° C.) overnight (15 hours). The mixture was filtered, with methylene chloride washings, and the filtrate was concentrated by rotoevaporation. The crude product was purified by flash chromatography on silica gel using 1:1 ethyl acetate-heptane to afford 1.2 g (50% yield) of 3-2 as a white solid: $^1$H NNR (CDCl$_3$) $\delta$5.26 (br s, 1 H) 4.77 (br s, 1 H), 4.28 (br s, 1 H) 3.22–3.09 (m, 10 H), 2.84 (s, 4 H), 2.05–1.61 (m, 8 H), 1.48 and 1.46 and 1.44 (3 s, 36 H) ; MS (ESI) m/z 744 (MH$^+$)

To a solution of 1–3 (0.2 g, (27 mmol)) in anhydrous dichloromethane (7 mL) was added triethylamine (75 ul, (54 mmol)). To this solution was added 3-2 (0.21 g, (30 mmol)). The reaction mixture was brought to reflux and allowed to stir for 10 minutes. The reaction mixture was cooled to room temperature, washed with water (2×2 mL), and dried with anhydrous sodium sulfate. The solvent was evaporated, and the crude material was purified by flash chromatography on silica gel(heptane, ethyl acetate, 1:1; Rf=0.37). A white foam was obtained (0.24 g, 74% yield). The purified product (0.245 g, (0.2 mmol)) was then deprotected with triflouroacetic acid/dichloromethane 1:1 (10 mL) for 20 minutes. After coevaporation with 1,2-dichloroethane the desired product 3-4 was obtained (0.2 g, 78% yield). $^1$H NMR (300 MHz, CDCl$_3$+CD$_3$OD, TMS=0), $\delta$3.99 (m, 1H) 3.50–2.95 (m, 4H), 2.28–1.78 (m, 10H), 1.52 (m, 4H), 1.27 (bs, 54H), 0.89 (t, 6H, J=7.0). ESIMS m/z (M$^+$) calcd for $C_{49}H_{102}N_6O_3$ 823, found 824 (M+1)$^+$.

Example 5

Cell Preparation and Protein Translation Arrest Assay Protocol

COS 7 cells (ATCC # CRL 1651) were plated at 1.5×10$^5$ cells/well in a 12 well plate format on the day before transfections began. All cultures were maintained at 37° C. in 5% CO$_2$. On the next day, the transfection mixes were prepared as follows: 4 $\mu$g of the target CAT plasmid (see Example 7), was combined with 10, 50, 100, or 400 nanomolar final phosphorothioate oligomer (synthesized by JBL Scientific, San Luis Obispo, Calif.) in 2 mL Opti-MEM® (Gibco/BRL, Gaithersburg, Md.) The oligomer/plasmid mixes were combined with 24 micrograms of lipid and gently vortexed. The final plasmid concentration was 2 $\mu$g/mL and the final lipid concentration was 12 mg/mL. The final result was four sets of transfection mixes tested in duplicate:

pG1040 plasmid+2519-1 oligomer+Lipofectin
pG1040 plasmid+2520-1 oligomer+Lipofectin
pG1040 plasmid+2519-1 oligomer+GC-001/GC-003 lipid mix
pG1040 plasmid+2520-1 oligomer+GC-001/GC-003 lipid mix Carbamothioate oligomer 2519-1 (5'-tag-ctt-cct-tag-ctc-ctg-cat) is a perfect antisense match to pG1040 from +1 to +21 on the CAT mRNA.

Carbamothioate oligomer 2520-1 (5'tag-ctt-ccg-caa-ctc-ttg-cat) is a 4 mismatch control carbamothioate, also from +1 to +21 on the CAT mRNA.

The culture medium was aspirated off and the cells were rinsed twice in one mL Opti-MEM® per well, and then 1 mL of transfection mix was added to each well. The cells were cultured in the transfection mix for 16 hours. The mix was removed and replaced with 1 mL of complete culture medium (DMEM plus 10% fetal bovine serum and 1/100 dilution of penicillin/streptomycin stock, all from Gibco/BRL, Gaithersburg, Md.) and the cells were incubated another 5 hours.

Cell lysates were prepared by rinsing twice in PBS and then treated with 0.5 mL of 1X Reporter Lysis Buffer (Promega, Madison, Wis.). The lysed cells were piptetted into 1.5 mL tubes and frozen in CO$_2$/EtOH once and thawed. The crude lysate was then clarified by microcentrifugation at 14,000 rpm for 10 minutes to pellet cell debris. The supernatant was recovered and assayed directly or frozen at −20° C.

The cell lysates were then assayed for CAT activity and the total protein concentration was determined as described below. The CAT activity was normalized to total protein and plotted as shown.

Chloramphenicol Acetyltransferase Assay

The following reaction mixture was prepared for each sample:

65 mL 0.23 M Tris, pH 8/0.5% BSA (Sigma, St. Louis, Mo.),
4 $\mu$L $^{14}$C-chloramphenicol, 50 nCi/$\mu$L (Dupont, Boston, Mass.), and
5 $\mu$L mg/mL n-butyryl coenzyme A (Pharmacia, Piscataway, N.J.)

A CAT activity standard curve was prepared by serially diluting CAT stock (Promega, Madison, Wis.) 1:1000, 1:10,000 and 1:90,000 in 0.25 M Tris, pH 8/0.5% BSA. The original stock CAT was at 7000 Units/mL. CAT lysate was then added in a labeled tube with Tris/BSA buffer for final volume of 50 $\mu$L.

Approximately 74 $\mu$L of reaction mixture was added to each tube, which was then incubated for approximately 1 hour in a 37° C. oven. The reaction was terminated by adding 500 $\mu$L pristane/mixed xylenes (2:1) (Sigma, St. Louis, Mo.) to each tube. The tubes were then vortexed for 2 minutes and spun for 5 minutes. Approximately, 400 $\mu$L of the upper phase was transferred to a scintillation vial with 5 mL Scintiverse (Fisher, Pittsburgh, Pa.). The sample was then counted in a scintillation counter (Packard).

Coomassie Protein Assay

The total protein content of the clarified cell lysates was determined by mixing 6 $\mu$L of each cell lysate to 300 $\mu$L of Coomassie protein assay reagent (Pierce, Rorkford, Md.) in the wells of an untreated microtiter assay plate. Concentration curve standards were prepared using 6 $\mu$L of 0, 75, 100, 200, 250, 400, 500, 1000, and 1500 mg/mL BSA stock solutions and 300 $\mu$L of the Coomassie reagent. The assay samples were allowed to sit for approximately 30 minutes before reading the optical absorbance at 570 nm in a microplate reader (Molecular Probes).

Results indicate that the combination of 1 and 4 was able to deliver oligo/plasmid better than lipofectamine. Virtually no effect was seen with lipofectamine from 0.01 to 0.1 micromolar. With the combination of 1 and 4, specific inhibition was very clear at 0.1 $\mu$M oligomer, and the trend from 0.01 to 0.1 indicates a reasonable dose response. From these data, it seemed that the combination of 1 and 4 was able to deliver carbamothioate oligonucleotides better than Lipofectin or plasmid alone.

The lack of activity against pG1040 by the control oligomer, 2520, indicates that this is an actual antisense effect, and not due to an artifact such as oligomer interference with plasmid delivery.

Example 6

Methods for FITC-Oligonucleotide Uptake Assay

The oligonucleotides used for the determination of cationic lipid mediated oligonucleotide uptake in all cell lines tested were:

3498-PS: 5'FITC-ggt-ata-tcc-agt-gat-ctt-ctt-ctc, all-carbamothioate backbone. This oligonucleotide has 23 negative charges on the backbone, and is considered 100% negatively charged.

3498: 5'FITC-ggt-ata-tcc-agt-gat-ctt-ctt-ctc, chimeric oligonucleotide. The underlined bases were linked by a carbamothioate backbone, while the other linkages in the oligomer consisted of alternating methylcarbamates and carbamate esters. The oligomer had 11 methylcarbamates, 7 carbamate esters, and 5 carbamothioate linkages. The total charge density was 57% of 3498-PS.

3793-2: 5'FITC-ggu-aua-ucc-agu-gau-cuu-cut, alternating methylcarbamates and carbamate esters backbone with all 2'-O-methyl groups on each ribose in the oligonucleotide. The total charge density was 50% of 3498-PS.

Oligonucleotides 3498-PS and 3498 stocks were at 300 μm, while the 3793-2 stock was at 440 μm.

The commercially available lipids used in the tests were:

| | | |
|---|---|---|
| Lipofectin ® | Lot#EF3101 | 1 mg/mL, as supplied by Gibco/BRL, (Gaithersburg, MD) |
| LipofectAMINE ® | Lot#EFN101 | 2 mg/mL, as supplied by Gibco/BRL (Gaithersburg, MD) |
| Transfectam ® | Lot#437121 | 1 mg dry, from Promega (Madison, WI) and resuspended in 100% ethanol. |

Every carbamate-based lipid used in these evaluations, as listed in the data tables, was at 1 mg/mL in 100% ethanol.

Tissue culture cell stocks, SNB-19 (human glioblastoma), C8161 (human tumor of unknown tissue origin), RD (human rhabdomyosarcoma, ATCC #CCL-136) HeLa (human adenocarinoma of the cervix, ATCC #CCL-2), HT1080 (human fibrosarcoma cells), and COS-7 (African green monkey kidney cells, ATCC #1651) were maintained in standard cell culture media: DMEM/F12 (1:1) mix from Mediatech, Lot#150901126, 10% fetal bovine serum from Gemini Bioproducts, Lot#A1089K, 100 units/mL, penicillin and 100 micrograms/mL streptomycin, from Mediatech, Lot#30001044 and 365 micrograms/mL L-glutamine. The cells were maintained under standard conditions at all times, 37°C, 5% $CO_2$ atmosphere prior to fixation and microscopic examination.

Each FITC-labeled oligonucleotide delivery determination was begun by plating the appropriate cells as listed in the data tables, into 16 well slides (Nunc #178599, glass microscope slide with 16 removable platic wells attached to the slide surface with a silicone gasket) according to standard tissue culture methods. Each cell line was plated at a starting density (approximately 20,000 cells/well) that allowed them to be healthy and 60–80% confluent one to two days after plating. The cells to were allowed to adhere to the glass and recover from the plating procedure in normal growth medium for 24 to 48 hours before beginning the transfection procedure.

Oligonucleotide transfection mixes were made up in Opti-MEM® without antibiotics as follows: 500 μL aliquotes of Opti-MEM® containing 0.25 μm of 3498-PS, 3498, or 3793-2 (2 μg of oligonucleotide) were pipetted into 1.5 mL Eppendorf tubes. Each cationic lipid or lipid mixture was then added to the oligonucleotide solution to give a final 9:1 or 6:1 ratio (18 or 12 μg of lipid total) of cationic lipid to oligonucleotide by weight, as listed in the data tables. The tubes were mixed by vortexing immediately after the addition of lipids.

Transfections were begun by rinsing the cells in 200 μL Opti-MEM® and then the cells were rinsed with Dulbecco's phosphate buffered saline (PBS) solution. Then 200 μL of each oligonucleotide transfection mix was then added directly to each well to begin each transfection reaction. Transfections continued for four to six hours.

The cells were then rinsed in PBS and fixed for ten minutes in 200 μL of 3.7% formaldehyde (Sigma, St. Louis, Mo.) to terminate the transfections and then rinsed again in PBS. The formaldehyde was quenched with 200 μL of 50 mM glycine (Sigma, St. Loius, Mo.) for ten minutes. Finally, the wells were then emptied by shaking out the glycine solution, the plastic chambers and silicone gasket were removed and the cells were covered with Fluoromount-G mounting medium (from Fisher, with photobleaching inhibitors) and a cover slip.

Intracellular fluorescence was evaluated under 200× magnification with a Nikon Labophot-2 microscope with an episcopic-fluorescence attachment. Using this equipement we could easily distinguish extracellular from nuclear and endosomal fluorescence. The cells were scored for uptake as follows: No nuclear fluorescence, 0; up to 20% fluorescent nuclei, 1; up to 40% fluorescent nuclei, 2; up to 60% fluorescent nuclei, 3; up to 80% fluorescent nuclei, 4; and up to 100% fluorescent nuclei, 5.

The results (FIG. 6) demonstrate varying delivery of oligonucleotides of varying charge densities to different cell types.

Example 7

Plasmids

The following plasmids were used in certain examples.

| | |
|---|---|
| pG1035: | Splicer CAT, inserted into a pRc/CMV vector |
| pG1036: | Wild-type CAT, inserted into a pRc/CMV vector |
| pG1040: | UCAT, inserted into a pRc/CMV vector |
| pGL2: | Luciferase expressing plasmid (Promega) |
| pSVb: | b-galactosidase expressing plasmid (Clonetech) |

A description of plasmids pG1035, pG1036 and pG1040 follows.

1. pG1035 (SplicerCAT) and pG1036 (wild-type CAT) and the sequences of the synthetic splice sites:

A. Sequence of the wild type CAT gene used to create plasmid pG1036:

```
                         +409 +410
                          1/2  1/2
GCC UAU UUC CCU AUU UCC CUA AAG GGU UUA UUG AGA AUA  [SEQ. ID. NO.1]
```

B. Full sequence of the intron inserted within the CAT coding sequence to create SplicerCAT and plasmid pG1035:

```
                          +409  1
                           1/21/2
... ACC UGG CCU AUU UCC CUA AAG gug agu gac uaa cua agu 39
                           1/2 cga cug cag acu agu cau ug(a) uug agu gua aca aga ccg  [SEQ. ID. NO.2]
                                87 +410
                                1/21/2
gau auc uuc gaa ccu cuc ucu cuc cag GGU UUA UUG AGA

...
```

The region of the CAT gene into which the intron was inserted is shown in sequence A above. Wild type CAT DNA (Pharmacia) was inserted into pRc/CMV (Invitrogen, San Diego, Calif.) to create plasmid pG1036. The sequence is shown as the mRNA. Bases 409 and 410 are labeled for comparison to pG1035. A synthetic intron, shown as sequence B above, was inserted into the CAT DNA to create plasmid pG1035. Mature mRNA sequences are shown uppercase, intronic sequences are lower case. The canonical guanosine of the splice donor is labeled +409, which corresponds to base 409 of the CAT open reading frame. The first base of the intron is labeled 1. The canonical branch-point adenosine is base 39 and the canonical intronic splice acceptor guanosine is base 87 of the intron. Base 410 marks the resumption of the CAT open reading frame. The sequences against which the oligomers are targeted are underlined. The consensus splice site bases are given in bold face italics (Smith et al., Ann. Rev. Genet. 23: 527, 1989; Green, Ann Rev. Genet. 20: 671, 1986).

The clone pG1035 was created using synthetic DNA PCR primers to create a Hind III-Spe I 5' fragment containing the first ⅔ of the open reading frame and half of the synthetic intron and an Spe I-Not I fragment containing the second half of the intron and the last ⅓ of the open reading frame. These were combined with Hind III-Not I cut pRc/CMV in a 3-way ligation to yield the final plasmid. The artificial CAT gene containing the intron is named SplicerCAT. References applicable to the foregoing include Smith et. al. supra and Green supra.

2. pG1040 (UCAT) 5' untranslated regions and amino terminus:

```
Wild-type CAT:
5'                              +1                                    3'
                                Met Glu Lys Lys Ile Ser Gly Tyr Thr Thr  [SEQ. ID. NO.3]
uuu uca gga gcu aag gaa gcu aaa aug gag aaa aaa auc acu gga uau acc acc  [SEQ. ID. NO.4]

pG1040, UCAT:

5'                              +1                                    3'
                                Met Glu Lys Lys Ile Ser Gly Tyr Thr Thr  [SEQ. ID. NO.5]
agu gca gga gcu aag gaa gcu acc aug gag aag aag auc acu                  [SEQ. ID. NO.6]

5' AUG site              3' AUG site
               3258-1                   3261-1
               3260-1                   3262-1
```

The sequences of wild type and pG1040 UCAT around the AUG start codon are shown. The target sites for the oligomers are named and underlined, and the numbers of the chimeric oligomers against each target site are shown beneath.

UCAT was made from wild-type CAT DNA (Pharmacia, piscataway, N.J.) using synthetic DNA PCR primers. The resulting fragment was cloned as a Hind III (5' end), Not I (3' end) fragment into the vector pRc/CMV (Invitrogen, San Diego, Calif.). The first adenosine of the open reading frame is designated +1. The amino acid changes between wild-type and pG1040 are conservative.

The summary of the invention described above is non-limiting and other features and advantages of the invention will be apparent from the following description of the preferred embodiments, and from the claims.

All references which have been cited below are hereby incorporated by reference in their entirety.

We claim:

1. A lipid having the structure:

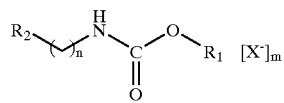

or a salt, or solvate, or enantiomers thereof wherein: (a) $R_1$ is a lipophilic moiety selected from the group consisting of a straight chain alkyl of 5 to about 24 carbon atoms, a straight chain alkenyl of 2 to about 24 carbon atoms, a symmetrical branched alkyl or alkenyl of about 10 to about 50 carbon atoms, a unsymmetrical branched alkyl or alkenyl of about 10 to about 50 carbon atoms, and $CH(R_3R_4)$, wherein $R_3$ and $R_4$ are independently a straight chain alkyl moiety of about 10 to about 30 carbon atoms, or a branched alkyl moiety of 3 to about 30 carbon atoms; (b) $R_2$ is selected from the group consisting of an amino acid residue having a positively charged group on the side chain, an alkylamine moiety of 3 to 10 carbon atoms, fluoroalkylamine moiety or a perfluoroalkylamine moiety of 1 to 6 carbon atoms, anarylamine moiety or an aralkylamine moiety of 5 to 10 carbon atoms, a guanidinium moiety, an enamine moiety, an aromatic or non-aromatic cyclic amine moiety of 3 to about 9 carbon atoms, an amidine moiety, an isothiourea moiety, a heterocyclic amine moiety, a heterocyclic moiety and an alkyl moiety of 1 to 6 carbon atoms substituted with a substituent selected from the group consisting of $NH_2$, $C(=O)NH_2$, $NHR_6$, $C(=O)NHR_6$, $NHR_6R_7$, or $C(=O)NHR_6R_7$, wherein $R_6$ and $R_7$ are independently selected from an alkyl moiety of 1 to 24 carbon atoms, an alkenyl moiety of 2 to 24 carbon atoms, an aryl moiety of 5 to 20 carbon atoms and an aralkyl moiety of 6 to 25 carbon atoms; (c) n is an integer from 1 to 8; (d) X is an anion or polyanion; and (e) m is a integer from 0 to a number equivalent to the positive charge(s present on the lipid.

2. A composition comprising a polyanionic macromolecule and a lipid according to claim 1.

3. A method of interfering with the expression of a protein in a cell comprising contacting a composition of claim 2 with the cell wherein an oligomer has a base sequence that is substantially complimentary to an RNA sequence in the cell that encodes the protein.

4. A kit for delivering a polyanionic macromolecule into a cell comprising a composition of claim 2.

\* \* \* \* \*